US012688928B2

(12) United States Patent
Liu et al.

(10) Patent No.: US 12,688,928 B2
(45) Date of Patent: Jul. 21, 2026

(54) LEARNING FROM PARTIALLY LABELED DATASETS FOR MEDICAL IMAGING ANALYSIS

(71) Applicant: Siemens Healthineers AG, Forchheim (DE)

(72) Inventors: Han Liu, Nashville, TN (US);
Zhoubing Xu, Princeton, NJ (US);
Sasa Grbic, Plainsboro, NJ (US)

(73) Assignee: Siemens Healthineers AG, Forchheim (DE)

( * ) Notice: Subject to any disclaimer, the term of this patent is extended or adjusted under 35 U.S.C. 154(b) by 245 days.

(21) Appl. No.: 18/589,490

(22) Filed: Feb. 28, 2024

(65) Prior Publication Data

US 2024/0296936 A1 Sep. 5, 2024

Related U.S. Application Data

(60) Provisional application No. 63/487,690, filed on Mar. 1, 2023.

(51) Int. Cl.
G16H 30/40 (2018.01)
G06V 10/44 (2022.01)
(Continued)

(52) U.S. Cl.
CPC ............. G16H 30/40 (2018.01); G06V 10/44 (2022.01); G06V 20/70 (2022.01); G16H 30/20 (2018.01); G06V 2201/07 (2022.01)

(58) Field of Classification Search
CPC ........ G16H 30/40; G16H 30/20; G16H 50/20; G06V 10/44; G06V 20/70; G06V 2201/07; G06V 2201/03; G06V 10/82
See application file for complete search history.

(56) References Cited

U.S. PATENT DOCUMENTS

2022/0405933 A1* 12/2022 Tajbakhsh .............. G06N 3/096
2024/0303984 A1* 9/2024 Sanchez-Matilla .... G06V 10/25
2025/0148771 A1* 5/2025 Kozma ............. G06F 18/24133

OTHER PUBLICATIONS

Nartey, O. T., Yang, G., Asare, S. K., Wu, J., Agyapong, D. A. Y., & Frempong, L. N. (2020). 3D Liver and Tumor Segmentation in CT Scans with Robust Self-Paced Learning. 2020 7th International Conference on Information Science and Control Engineering (ICISCE), 1520-1529. (Year: 2020).*

(Continued)

*Primary Examiner* — Stephen R Koziol
*Assistant Examiner* — Michael Kim Maiden

(57) ABSTRACT

Systems and methods for performing a medical imaging analysis task are provided. One or more input medical images are received. A medical imaging analysis task is performed based on the one or more input medical images using a machine learning based model. Results of the medical imaging analysis task are output. The machine learning based model is trained by receiving one or more training medical images and ground truth labels identifying one or more anatomical objects in the one or more training medical images, training the machine learning based model for performing the medical imaging analysis task based on the one or more training medical images and the ground truth labels, generating pseudo labels identifying the one or more anatomical objects in the one or more training medical images using the trained machine learning based model, and fine-tuning the trained machine learning based model for performing the medical imaging analysis task based on the one or more training medical images, the ground truth labels, and the generated pseudo labels.

17 Claims, 26 Drawing Sheets

(51) Int. Cl.
G06V 20/70 (2022.01)
G16H 30/20 (2018.01)

(56) References Cited

OTHER PUBLICATIONS

Zhou et al., "Prior-aware neural network for partially-supervised multi-organ segmentation", Proceedings of the IEEE/CVF International Conference on Computer Vision, 2019, 10 pgs.

Fang et al., "Multi-organ segmentation over partially labeled datasets with multi-scale feature abstraction", IEEE Transactions on Medical Imaging, 2020, pp. 1-11.

Shi et al., "Marginal loss and exclusion loss for partially supervised multi-organ segmentation", Medical Image Analysis, 2020, pp. 1-11.

Huang et al., "Multi-organ segmentation via co-training weight-averaged models from few-organ datasets", International Conference on Medical Image Computing and Computer-Assisted Intervention, 2020, pp. 1-10.

Feng et al., "MS-KD: Multi-Organ Segmentation with Multiple Binary-Labeled Datasets", arXiv:2108.02559v1, 2021, pp. 1-9.

Zhang et al., "DoDNet: Learning to segment multi-organ and tumors from multiple partially labeled datasets", Proceedings of the IEEE/CVF Conference on Computer Vision and Pattern Recognition, 2021, pp. 1-10.

Chen et al., "Semi-supervised semantic segmentation with cross pseudo supervision", Proceedings of the IEEE/CVF Conference on Computer Vision and Pattern Recognition, 2021, pp. 1-10.

Northcutt et al., "Confident learning: Estimating uncertainty in dataset labels", Journal of Artificial Intelligence Research, 2021, 24 pgs.

Hinton et al., "Distilling the knowledge in a neural network", arXiv:1503.02531, 2015, pp. 1-9.

Landman et al., "Multi-atlas labeling beyond the cranial vault—Workshop and Challenge," 2023 NIH Policy for Data Management Sharing, retrieved online https://www.synapse.org/syn3193805/wiki/89480, 2015, 6 pgs.

Kavur et al., "CHAOS challenge-combined (CT-MR) healthy abdominal organ segmentation," Medical Image Analysis, 2021, pp. 1-10.

Ma et al., "Fast and low-GPU-memory abdomen CT organ segmentation: the FLARE challenge," Medical Image Analysis, 2022, pp. 1-12.

Ma et al., "AbdomenCT-1K: Is abdominal organ segmentation a solved problem?", IEEE Transactions on Pattern Analysis and Machine Intelligence, 2021, pp. 1-19.

Sahiner et al., "Deep learning in medical imaging and radiation therapy", Medical Physics, 2019, pp. e1-e36.

Schoppe et al., "Deep learning-enabled multi-organ segmentation in whole-body mouse scans," Nature Communications, 2020, pp. 1-14.

Isensee et al., "nnU-Net: a self-configuring method for deep learning-based biomedical image segmentation", Nature Methods, 2021, 14 pgs.

Gibson et al., "Automatic Multi-organ segmentation on abdominal CT with dense V-networks," IEEE Transactions on Medical Imaging, 2018, pp. 1-29.

Wang et al., "Abdominal multi-organ segmentation with organ-attention networks and statistical fusion", Medical Image Analysis, 2019, pp. 88-102.

Tang et al., "High-resolution 3D abdominal segmentation with random patch network fusion", Medical Image Analysis, 2021, pp. 1-15.

Lee et al., "3D UX-Net: A large kernel volumetric convNet modernizing hierarchical transformer for medical image segmentation", arXiv:2209.15076v4, 2023, pp. 1-15.

Deng et al., "ImageNet: A large-scale hierarchical image database", EEE Conference on Computer Vision and Pattern Recognition, 2009, pp. 1-8.

Liu et al., "Universal segmentation of 33 anatomies", arXiv:2203.02098v1, 2022, pp. 1-10.

Dmitriev et al., "Learning multi-class segmentations from single-class datasets", Proceedings of the IEEE/CVF Conference on Computer Vision and Pattern Recognition, 2019, pp. 9501-9511.

Gonzalez et al., "Multi-structure segmentation from partially labeled datasets. Application to body composition measurements on CT scans", Image Analysis for Moving Organ, Breast, and Thoracic Images, 2018, 10 pgs.

Petit et al., "Iterative confidence relabeling with deep convNets for organ segmentation with partial labels", Computerized Medical Imaging and Graphics, 2021, pp. 1-14.

Deng et al., "Omni-Seg: A scale-aware dynamic network for renal pathological image segmentation", IEEE Transactions on Biomedical Engineering, 2023, pp. 1-26.

Wu et al., "TGNET: A task-guided network architecture for multi-organ and tumour segmentation from partially labelled datasets", 2022 IEEE 19th International Symposium on Biomedical Imaging (ISBI), 2022, pp. 1-5.

Lee et al., 3D UX-Net: A large kernel volumetric con-vNet modernizing hierarchical transforer for medicl image segmentation, arXiv:2209.15076v4, 2023, pp. 1-15.

Lee et al., "Pseudo-Label: The simple and efficient semi-supervised learning method for deep neural networks," Computer Science, 2013, pp. 1-6.

Yang et al., "ST++: Make self-training work better for semi-supervised semantic segmentation", arXiv:2106.05095v1, 2021, pp. 1-16.

Chaitanya et al., "Local contrastive loss with pseudo-label based self-training for semi-supervised medical image segmentation", Medical Image Analysis, 2023, pp. 1-12.

Zou et al., "Confidence regularized self-training", Proceedings of the IEEE/CVF International Conference on Computer Vision, 2019, pp. 5982-5991.

Xie et al., "Unsupervised domain adaptation for medical image segmentation by disentanglement learning and self-training", IEEE Transactions on Medical Imaging, 2022, pp. 1-11.

Shin et al., "COSMOS: Cross-modality unsupervised domain adaptation for 3d medical image segmentation based on target-aware domain translation and iterative selftraining", arXiv:2203.16557v2, 2023, pp. 1-10.

Dong et al., "Unsupervised domain adaptation in semantic segmentation based on pixel alignment and self-training (PAST)", arXiv:2109.14219v1, 2021, pp. 1-6.

Liu et al., "Enhancing data diversity for self-training based unsupervised cross-modality vestibular Schwannoma and cochlea segmentation", arXiv:2209.11879v2, 2022, pp. 1-10.

Wang et al., "Cost-effective active learning for deep image classification", IEEE Transactions on Circuits and Systems for Video Technology, 2017, pp. 2591-2600.

Kostic et al., "Pseudo-labels are all you need", arXiv:2208.09243v1, 2022, pp. 1-6.

Song et al., "Learning from synthetic images via active pseudo-labeling", IEEE Transactions on Image Processing, 2020, pp. 1-14.

Arazo et al., "Pseudo-labeling and confirmation bias in deep semi-supervised learning", 2020 International Joint Conference on Neural Networks, 2020, pp. 1-8.

Wang et al., "Self-tuning for data-efficient deep learning", International Conference on Machine Learning, 2021, pp. 1-11.

Zhang et al., "Prototypical pseudo label denoising and target structure learning for domain adaptive semantic segmentation (supplementary material)" Proceedings of the IEEE/CVF Conference on Computer Vision and Pattern Recognition, 2021, 8 pgs.

Ruff et al., "Deep one-class classification", International Conference on Machine Learning, 2018, pp. 1-10.

Antonelli et al., "The medical segmentation decathlon", Nature Communications, 2022, pp. 1-13.

Heller et al., "The state of the art in kidney and kidney tumor segmentation in contrast-enhanced CT imaging: Results of the KiTS19 challenge", arXiv:1912.1054v2, 2020, pp. 1-24.

Ji et al., "AMOS: A large-scale abdominal multi-organ benchmark for versatile medical image segmentation", Advances in Neural Information Processing Systems, 2022, pp. 1-11.

(56) References Cited

OTHER PUBLICATIONS

Ronneberger et al., "U-Net: Convolutional networks for biomedical image segmentation", arXiv:1505.04597v1, 2015, pp. 1-8.
Paszke et al., "Pytorch: An imperative style, high-performance deep learning library", Advances in Neural Information Processing Systems, 2019, pp. 1-12.
Cardoso et al., "MONAI: An open-source framework for deep learning in healthcare", arXiv:2211.02701v1, 2022, pp. 1-25.
Hu et al., "Knowledge distillation from multi-modal to mono-modal segmentation networks", International Conference on Medical Image Computing and Computer-Assisted Intervention, 2020, pp. 772-781.
Ye et al., "UniSeg: A prompt-driven universal segmentation model as well as a strong representation learner", arXiv:2304.03493v1, 2023, pp. 1-13.
Liu et al., "CLIP-driven universal model for organ segmentation and tumor detection", arXiv:2301.00785v5, 2023, pp. 1-24.
Ulrich et al., "MultiTalent: A multi-dataset approach to medical image segmentation", arXiv:2303.14444v2, 2023, pp. 1-13.
Li et al., "Grounded language-image pretraining", arXiv:2112.03857v2, 2022, pp. 1-20.
Kirillov et al., "Segment anything", arXiv:2304.02643v1, 2023, pp. 1-30.

* cited by examiner

Figure 3:
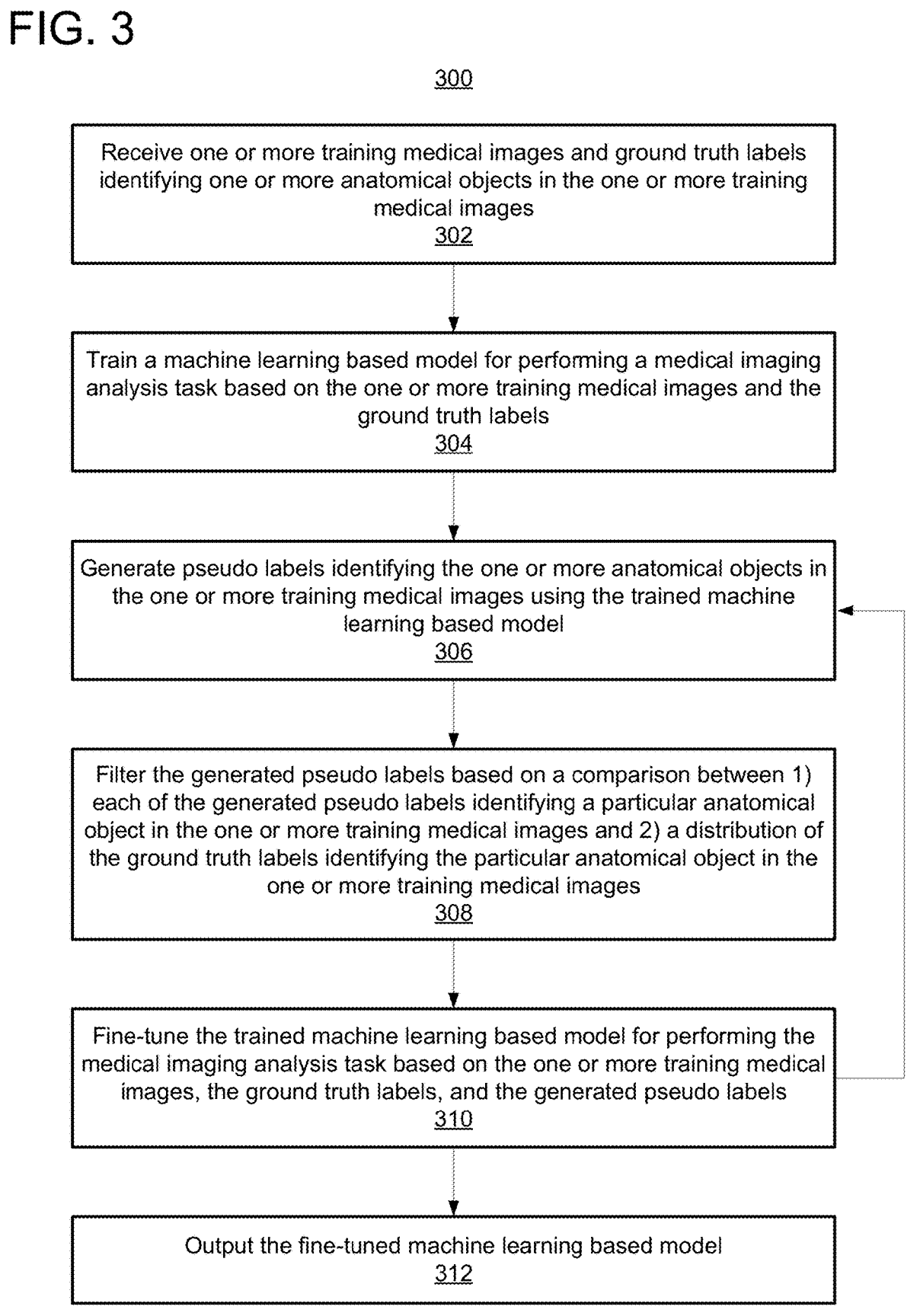

Receive one or more training medical images and ground truth labels identifying one or more anatomical objects in the one or more training medical images
302

Train a machine learning based model for performing a medical imaging analysis task based on the one or more training medical images and the ground truth labels
304

Generate pseudo labels identifying the one or more anatomical objects in the one or more training medical images using the trained machine learning based model
306

Filter the generated pseudo labels based on a comparison between 1) each of the generated pseudo labels identifying a particular anatomical object in the one or more training medical images and 2) a distribution of the ground truth labels identifying the particular anatomical object in the one or more training medical images
308

Fine-tune the trained machine learning based model for performing the medical imaging analysis task based on the one or more training medical images, the ground truth labels, and the generated pseudo labels
310

Output the fine-tuned machine learning based model
312

Algorithm 1: Pseudocode of COSST input : Partially labeled datasets $\mathcal{D}_{PL}$,
         hyperparameters: $\tau$ output: Parameters of the unified model $\theta$

Figure 5:
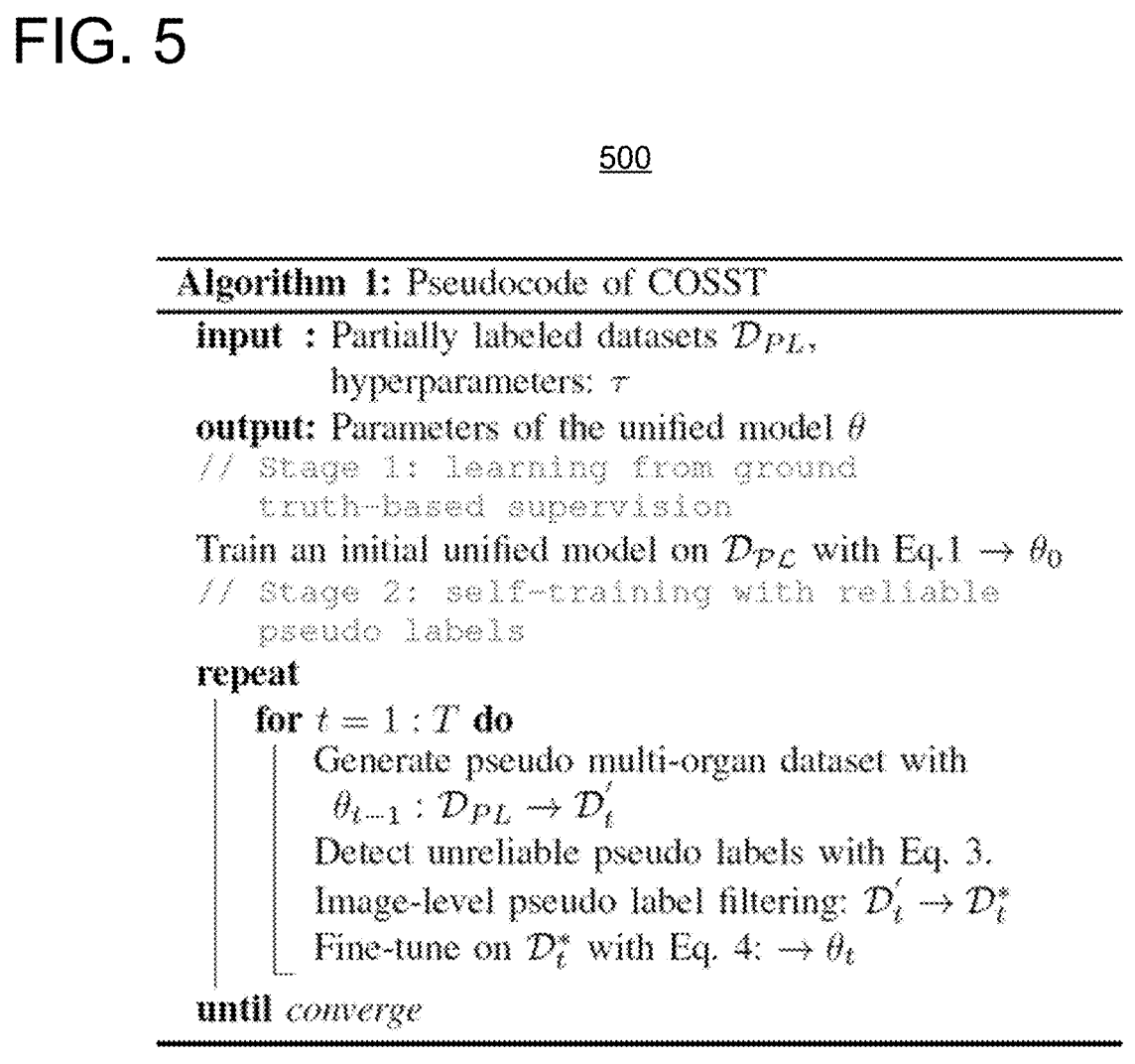

// Stage 1: learning from ground
     truth-based supervision

Train an initial unified model on $\mathcal{D}_{PL}$ with Eq.1 $\rightarrow \theta_0$ // Stage 2: self-training with reliable
     pseudo labels repeat for $t = 1 : T$ do

Generate pseudo multi-organ dataset with
           $\theta_{t-1} : \mathcal{D}_{PL} \rightarrow \mathcal{D}'_t$ Detect unreliable pseudo labels with Eq. 3.

Image-level pseudo label filtering: $\mathcal{D}'_t \rightarrow \mathcal{D}^*_t$ Fine-tune on $\mathcal{D}^*_t$ with Eq. 4: $\rightarrow \theta_t$ until *converge*

---

700

Receive one or more input medical images
702

Perform a medical imaging analysis task based on the one or more input medical images using a machine learning based model, wherein the machine learning based model is trained according to method 300 of Figure 3
704

Output results of the medical imaging analysis task
706

800

| Dataset | # train / valid / test | # organs | annotated organs |
|---|---|---|---|
| KiTS19 | 84 / 21 / 105 | 2 | left kidney, right kidney |
| Spleen (MSD) | 16 / 4 / 21 | 1 | spleen |
| Pancreas (MSD) | 112 / 28 / 140 | 1 | pancreas |
| Liver (MSD) | 52 / 13 / 66 | 1 | liver |
| BTCV | - / - / 30 | 5 | left kidney, right kidney, spleen, pancreas, liver, other structures |
| AMOS2022 | - / - / 300 | 5 | left kidney, right kidney, spleen, pancreas, liver, other structures |

| Task | Dataset | spacing (mm) | # train / valid / test | # organs | annotated organs |
|---|---|---|---|---|---|
| Task 2 | Bowel 1 | 2 × 2 × 2 | 104 / 41 / 63 | 2 | duodenum, small bowel |
| | Bowel 2 | 2 × 2 × 2 | 104 / 41 / 63 | 3 | large bowel, sigmoid, rectum |
| Task 3 | Pelvic 1 | 2 × 2 × 2 | 568 / 72 / 72 | 6 | bladder, prostate, rectum, femur (L), femur (R), seminal vesicle |
| | Pelvic 2 | 2 × 2 × 2 | 128 / 16 / 16 | 1 | uterus |
| Task 4 | Eye 1 | 1 × 1 × 1 | 124 / 62 / 63 | 3 | chiasm, optic nerve (L), optic nerve (R) |
| | Eye 2 | 1 × 1 × 1 | 125 / 62 / 63 | 4 | lens (L), lens (R), eyeball (L), eyeball (R) |

| Methods | Left kidney (P) | | | Right kidney (P) | | | Spleen (P) | | | Pancreas (P) | | | Liver (P) | | |
|---|---|---|---|---|---|---|---|---|---|---|---|---|---|---|---|
| | DSC | HD95 | ASD | DSC | HD95 | ASD | DSC | HD95 | ASD | DSC | HD95 | ASD | DSC | HD95 | ASD |
| Multi-Nets | 96.11* | 6.20* | 1.27* | 96.20* | 3.13 | 0.58* | 91.59* | 28.15* | 3.72* | 77.23† | 6.88* | 1.40 | 94.81* | 7.54* | 1.28 |
| TAL | 96.13* | 4.19† | 0.81 | 96.22* | 4.05† | 0.66 | 93.72 | 2.97 | 0.82 | 76.36† | 6.37 | 1.43* | 94.86 | 6.10 | 1.31 |
| ME | 96.16* | 1.65* | 0.44* | 95.87* | 7.56* | 1.27* | 94.09* | 2.38 | 0.77† | 75.99* | 6.01* | 0.77* | 94.70 | 7.45 | 1.90 |
| PLT | 95.97† | 3.29* | 0.81* | 96.21* | 2.46 | 0.55* | 93.41† | 34.85† | 3.97* | 77.69 | 6.82† | 1.32 | 95.24 | 6.13 | 1.10 |
| Co-train | 93.89 | 4.99 | 0.91 | 96.55* | 4.79 | 0.70 | 93.09 | 42.06 | 5.24* | 77.50 | 6.22† | 1.71 | 95.24 | 5.10† | 0.96 |
| DoDNet | 95.33* | 9.23* | 1.31* | 95.12* | 16.13* | 3.43* | 93.75 | 15.44 | 2.23 | 79.09† | 3.84 | 1.17* | 93.65 | 11.26* | 2.01* |
| COSST | 96.55 | 2.76 | 0.51 | 96.48 | 2.03 | 0.42 | 94.40 | 1.45 | 0.54 | 77.98 | 3.82 | 1.29 | 95.22 | 3.78 | 1.18 |

| Methods | Left kidney (F1) | | | Right kidney (F1) | | | Spleen (F1) | | | Pancreas (F1) | | | Liver (F1) | | |
|---|---|---|---|---|---|---|---|---|---|---|---|---|---|---|---|
| | DSC | HD95 | ASD | DSC | HD95 | ASD | DSC | HD95 | ASD | DSC | HD95 | ASD | DSC | HD95 | ASD |
| Multi-Nets | 86.34 | 21.61 | 4.94 | 84.58 | 16.08 | 5.82 | 87.72 | 29.36 | 6.21 | 73.11 | 22.06 | 4.14 | 94.80 | 7.19 | 1.18 |
| TAL | 87.03 | 12.74 | 2.48 | 83.51 | 15.52 | 5.42 | 98.02 | 12.15 | 2.28 | 73.86 | 7.77 | 1.76 | 95.99 | 8.01 | 1.05 |
| ME | 85.82 | 0.52 | 1.70 | 84.50 | 10.20 | 2.61 | 90.98 | 14.25 | 2.91 | 74.87 | 21.77 | 3.03 | 95.96 | 10.15 | 1.80 |
| PLT | 87.29 | 10.55 | 2.42 | 84.13 | 15.46 | 5.20 | 88.00 | 55.87 | 8.17 | 75.38 | 11.24 | 2.13 | 95.82 | 3.05 | 0.62 |
| Co-train | 87.40 | 11.74 | 3.01 | 85.04 | 10.34 | 4.07 | 88.53 | 32.43 | 8.82 | 75.95 | 10.81 | 1.90 | 95.82 | 5.18 | 0.77 |
| DoDNet | 86.63 | 14.39 | 2.86 | 84.89 | 18.77 | 4.98 | 88.94 | 22.01 | 4.50 | 76.51 | 7.34 | 1.61 | 94.45 | 20.44 | 3.58 |
| COSST | 86.05 | 9.30 | 2.44 | 86.94 | 7.78 | 1.62 | 92.34 | 4.14 | 1.35 | 77.17 | 3.90 | 1.56 | 98.28 | 3.86 | 0.71 |

| Methods | Left kidney (F2) | | | Right kidney (F2) | | | Spleen (F2) | | | Pancreas (F2) | | | Liver (F2) | | |
|---|---|---|---|---|---|---|---|---|---|---|---|---|---|---|---|
| | DSC | HD95 | ASD | DSC | HD95 | ASD | DSC | HD95 | ASD | DSC | HD95 | ASD | DSC | HD95 | ASD |
| Multi-Nets | 87.10 | 17.26 | 3.66 | 83.39 | 13.57 | 2.41 | 81.62 | 38.40 | 7.15 | 66.72 | 29.23 | 5.48 | 92.25 | 7.96 | 1.40 |
| TAL | 88.13 | 8.98 | 1.40 | 86.08* | 11.34† | 2.60* | 87.36 | 13.24 | 2.73 | 67.87 | 16.99 | 3.24 | 93.47 | 6.30 | 1.33 |
| ME | 86.75 | 9.90 | 3.98 | 86.31* | 9.33 | 1.56 | 89.35 | 10.01 | 2.73 | 70.33 | 25.30 | 6.74 | 93.40 | 10.80 | 2.92 |
| PLT | 88.63 | 8.72 | 1.27 | 88.18 | 8.70 | 3.84 | 88.65 | 38.60 | 5.10 | 72.40 | 11.00 | 2.03 | 93.51 | 6.26 | 1.12 |
| Co-train | 88.71 | 11.99 | 1.67 | 87.75 | 11.17 | 1.88 | 88.56 | 67.60 | 11.53 | 71.61 | 17.29 | 2.71 | 93.22 | 6.49 | 1.10 |
| DoDNet | 88.26 | 16.81 | 2.27 | 87.71 | 22.55 | 2.09 | 88.17 | 28.23 | 5.32 | 67.73 | 12.72 | 2.32 | 92.96 | 10.50 | 2.28 |
| COSST | 89.40 | 7.75 | 0.98 | 88.96 | 6.75 | 0.95 | 91.64 | 4.14 | 0.96 | 72.46 | 7.49 | 1.53 | 94.40 | 5.35 | 1.69 |

| Methods | Average (P) | | | Average (F1) | | | Average (F2) | | | Average (all) | | |
|---|---|---|---|---|---|---|---|---|---|---|---|---|
| | DSC | HD95 | ASD | DSC | HD95 | ASD | DSC | HD95 | ASD | DSC | HD95 | ASD |
| Multi-Nets | 91.18 | 9.98 | 1.65 | 85.31* | 19.26† | 4.46* | 82.25* | 21.30* | 4.02* | 86.25 | 16.85 | 3.38 |
| TAL | 91.46 | 4.74 | 1.01 | 86.08* | 11.34† | 2.60* | 84.47* | 11.01* | 2.05* | 87.34 | 8.90 | 1.89 |
| ME | 91.36 | 5.01 | 1.03 | 86.31* | 13.18† | 2.49* | 85.57* | 13.38* | 4.04* | 87.75 | 10.72 | 2.52 |
| PLT | 91.70 | 10.71 | 1.56 | 86.12† | 19.35† | 3.71* | 86.47* | 14.66* | 2.28* | 88.10 | 11.91 | 2.51 |
| Co-train | 91.61 | 12.63 | 1.80 | 86.54† | 18.10* | 3.71* | 85.7* | 22.91* | 3.78* | 88.04 | 17.88 | 3.10 |
| DoDNet | 91.39 | 11.58 | 2.01 | 86.48* | 16.61* | 3.47* | 83.96* | 18.16* | 3.17* | 87.61 | 15.45 | 2.98 |
| COSST | 92.11 | 3.57 | 0.79 | 87.26 | 6.23 | 1.48 | 87.37 | 6.29 | 1.12 | 89.08 | 5.36 | 1.16 |

| Methods | Duodenum | | Small Bowel | | Large Bowel | | Sigmoid | | Rectum | | Average | |
|---|---|---|---|---|---|---|---|---|---|---|---|---|
| | DSC | ASD | DSC | ASD | DSC | ASD | DSC | ASD | DSC | ASD | DSC | ASD |
| Multi-Nets | 70.57 | 2.82 | 83.70* | 2.70* | 81.83† | 3.80† | 66.12* | 7.66 | 73.31 | 4.58 | 75.11 | 4.32 |
| TAL [14] | 63.82* | 3.20† | 85.12* | 2.38† | 84.05* | 3.32* | 68.13* | 6.52 | 74.46 | 3.42 | 75.12 | 3.76 |
| ME [15] | 70.59* | 2.88* | 85.80* | 2.66* | 84.93* | 3.08* | 70.24* | 7.46 | 75.60 | 3.88† | 77.43 | 4.00 |
| PLT [16] | 71.51 | 2.56 | 84.79* | 2.32 | 83.93* | 3.12 | 68.27 | 6.44† | 75.60 | 3.28* | 76.82 | 3.54 |
| Co-train [17] | 71.95 | 2.52† | 85.54* | 2.16 | 84.72† | 3.04 | 69.94 | 5.94 | 76.06 | 3.88 | 77.64 | 3.52 |
| MS-KD [18] | 65.16* | 5.02* | 83.06* | 3.54* | 80.76* | 7.08* | 66.06* | 12.70† | 70.19† | 5.42* | 73.04 | 6.76 |
| DoDNet [19] | 42.97* | 98.44* | 84.39* | 3.00* | 83.28* | 5.50† | 67.16* | 9.46* | 56.06* | 102.84 | 66.77 | 43.84 |
| COSST (ours) | 71.94 | 2.74 | 86.45 | 2.30 | 86.07 | 3.02 | 70.84 | 5.72 | 76.06 | 3.60 | 78.27 | 3.48 |
| Upper bound | 74.41 | 2.84 | 86.92 | 2.28 | 86.09 | 3.04 | 73.67 | 5.28 | 77.04 | 3.28 | 79.63 | 3.34 |

| Methods | Bladder | | Prostate | | Rectum | | Femur (L) | | Femur (R) | | Sem.Ves | | Uterus | | Average | |
|---|---|---|---|---|---|---|---|---|---|---|---|---|---|---|---|---|
| | DSC | ASD | DSC | ASD | DSC | ASD | DSC | ASD | DSC | ASD | DSC | ASD | DSC | ASD | DSC | ASD |
| Multi-Nets | 87.80* | 6.88* | 77.51 | 2.16 | 83.42† | 2.16 | 93.15† | 0.78* | 93.15* | 0.96 | 71.40† | 1.58† | 78.59 | 3.98 | 83.57 | 2.74 |
| TAL [14] | 87.82† | 5.66† | 73.88† | 2.30* | 82.06 | 2.28* | 94.78 | 1.26 | 94.53 | 0.98 | 65.25 | 1.90 | 75.37† | 3.74 | 81.96 | 2.30 |
| ME [15] | 88.97† | 1.82* | 79.56 | 2.28* | 84.62* | 2.76* | 94.11* | 1.08* | 93.28* | 1.24* | 73.64 | 1.50* | 79.65 | 3.96 | 84.83 | 2.10 |
| PLT [16] | 88.10 | 3.80 | 77.31 | 6.06 | 83.34 | 2.46 | 93.80 | 2.92 | 93.45 | 2.62* | 73.34 | 1.40 | 75.79 | 4.52 | 83.59 | 3.40 |
| Co-train [17] | 80.71 | 3.10 | 79.20 | 2.10 | 85.84 | 2.12 | 95.01 | 0.86 | 94.62 | 0.98* | 72.58 | 1.42 | 73.91 | 4.44 | 84.41 | 2.14 |
| MS-KD [18] | 78.55† | 7.86 | 69.84 | 3.14 | 77.08 | 9.36 | 91.90† | 4.82* | 92.65* | 2.70* | 46.02 | 2.64 | 74.16 | 7.34 | 75.87 | 5.40 |
| DoDNet [19] | 88.09† | 5.98† | 77.55† | 4.26* | 85.22† | 2.34* | 62.44* | 90.32† | 63.23† | 88.64* | 73.77† | 3.90* | 79.35 | 4.16* | 75.67 | 28.50 |
| COSST (ours) | 89.43 | 1.54 | 79.64 | 2.20 | 85.84 | 2.06 | 95.14 | 0.82 | 94.59 | 0.96 | 73.50 | 1.40 | 78.99 | 3.72 | 85.30 | 1.82 |

| Methods | Chiasm | | ON (L) | | ON (R) | | Len (L) | | Len (R) | | Eyeball (L) | | Eyeball (R) | | Average | |
|---|---|---|---|---|---|---|---|---|---|---|---|---|---|---|---|---|
| | DSC | ASD | DSC | ASD | DSC | ASD | DSC | ASD | DSC | ASD | DSC | ASD | DSC | ASD | DSC | ASD |
| Multi-Nets | 48.76† | 1.24 | 65.54* | 0.82 | 66.55† | 0.82† | 76.66 | 0.56 | 76.53 | 0.49 | 92.57 | 0.54 | 92.59 | 0.54 | 74.17 | 0.72 |
| TAL [14] | 44.98* | 1.18 | 61.27* | 0.84 | 62.99 | 0.80 | 62.73* | 0.55* | 70.23* | 0.55* | 91.47* | 0.55* | 91.87* | 0.55* | 69.56 | 0.76 |
| ME [15] | 49.56* | 1.39* | 66.38* | 0.86* | 67.21* | 0.83* | 77.00 | 0.53 | 77.70 | 0.50* | 91.86* | 0.74* | 91.82* | 0.55* | 74.52 | 0.77 |
| PLT [16] | 49.58† | 1.21†† | 66.35 | 0.81 | 67.86 | 0.79† | 77.07 | 0.55 | 77.79 | 0.50 | 92.57† | 0.55† | 92.59 | 0.55 | 74.72 | 0.71 |
| Co-train [17] | 49.60 | 1.25 | 66.57 | 0.80 | 67.45 | 0.78 | 76.84 | 0.55 | 77.41 | 0.47 | 92.52† | 0.55* | 92.78 | 0.52* | 74.44 | 0.70 |
| MS-KD [18] | 47.07* | 1.87* | 57.63* | 1.50* | 58.17* | 1.45* | 76.37 | 0.81* | 77.25 | 0.55* | 92.17 | 0.55 | 91.80* | 0.73* | 71.50 | 1.07 |
| DoDNet [19] | 47.86 | 1.32 | 41.40* | 17.47* | 43.54* | 17.32* | 43.91* | 33.23* | 51.47* | 28.43* | 60.54* | 26.52* | 61.80* | 26.16* | 50.07 | 21.49 |
| COSST (ours) | 50.55 | 1.26 | 67.17 | 0.81 | 67.89 | 0.79 | 76.89 | 0.55 | 77.99 | 0.48 | 92.31 | 0.58 | 92.52 | 0.56 | 75.48 | 0.71 |

| pseudo label | image-level | voxel-level | DSC (%) | ASSD (mm) |
|---|---|---|---|---|
| | | | 77.43 | 4.00 |
| ✓ | | | 77.85 | 3.96 |
| ✓ | ✓ | | 78.27 | 3.48 |
| ✓ | | ✓ | 77.74 | 3.98 |
| ✓ | ✓ | ✓ | 77.91 | 3.80 |

2100

2200

LEARNING FROM PARTIALLY LABELED DATASETS FOR MEDICAL IMAGING ANALYSIS

CROSS-REFERENCE TO RELATED APPLICATIONS

This application claims the benefit of U.S. Provisional Application No. 63/487,690, filed Mar. 1, 2023, the disclosure of which is herein incorporated by reference in its entirety.

TECHNICAL FIELD

The present invention relates generally to machine learning based medical imaging analysis, and in particular to learning from partially labeled datasets for medical imaging analysis.

BACKGROUND

Multi-organ segmentation in CT (computed tomography) images plays an important role in many biomedical tasks. For example, multi-organ segmentation is important in radiotherapy treatment planning since it facilitates accurate delineation of organs that are to be avoided during irradiation. Recently, deep learning-based methods have been proposed using a single machine learning-based model for multi-organ segmentation of organs. However, such machine learning-based models are typically trained using large-scale densely annotated datasets, which are difficult to obtain in the medical domain, especially with all organs of interest annotated in that single dataset.

In practice, organs are typically individually annotated in respective datasets, referred to as partially labeled datasets. To utilize such partially labeled datasets, conventionally, each of a plurality of machine learning-based models are trained for segmenting an organ using one of the partially labeled datasets. At inference, each of the plurality of machine learning-based models are applied and the outputs of the deep learning-based models are combined. However, such conventional approaches have slower inference speeds and higher storage requirements, while also requiring extra post-processing steps to address conflicting voxel predictions.

BRIEF SUMMARY OF THE INVENTION

In accordance with one or more embodiments, systems and methods for performing a medical imaging analysis task are provided. One or more input medical images are received. A medical imaging analysis task is performed based on the one or more input medical images using a machine learning based model. Results of the medical imaging analysis task are output. The machine learning based model is trained by receiving one or more training medical images and ground truth labels identifying one or more anatomical objects in the one or more training medical images, training the machine learning based model for performing the medical imaging analysis task based on the one or more training medical images and the ground truth labels, generating pseudo labels identifying the one or more anatomical objects in the one or more training medical images using the trained machine learning based model, and fine-tuning the trained machine learning based model for performing the medical imaging analysis task based on the one or more training medical images, the ground truth labels, and the generated pseudo labels.

In one embodiment, the machine learning based model is further trained by filtering the generated pseudo labels based on a comparison between 1) each of the generated pseudo labels identifying a particular anatomical object in the one or more training medical images and 2) a distribution of the ground truth labels identifying the particular anatomical object in the one or more training medical images. The trained machine learning based model is fine-tuned for performing the medical imaging analysis task based on the filtered pseudo labels. In one embodiment, the filtering comprises determining a feature representation of each of the generated pseudo labels using a feature extractor model of the machine learning based model. A distance between a) the feature representation of each of the generated pseudo labels identifying the particular anatomical object in the one or more training medical images and b) the distribution of the ground truth labels identifying the particular anatomical object in the one or more training medical images is determined. The generated pseudo labels are filtered based on a comparison between the distances and a threshold. In one embodiment, the generating, the filtering, and the fine-tuning are repeated for a plurality of iterations.

In one embodiment, the trained machine learning based model is fine-tuned to maximize an overlap between a predicted location of the one or more anatomical objects and a location defined in the ground truth labels. In one embodiment, the trained machine learning based model is fine-tuned to maximize an overlap between a predicted location of unlabeled anatomical objects and a location defined in the pseudo labels for the unlabeled anatomical objects.

In one embodiment, the medical imaging analysis task is segmentation.

In accordance with one or more embodiments, systems and method for training a machine learning based model are provided. One or more training medical images and ground truth labels identifying one or more anatomical objects in the one or more training medical images are received. A machine learning based model is trained for performing a medical imaging analysis task based on the one or more training medical images and the ground truth labels. Pseudo labels identifying the one or more anatomical objects in the one or more training medical images are generated using the trained machine learning based model. The trained machine learning based model is fine-tuned for performing the medical imaging analysis task based on the one or more training medical images, the ground truth labels, and the generated pseudo labels. The fine-tuned machine learning based model is output.

In one embodiment, the generated pseudo labels are filtered based on a comparison between 1) each of the generated pseudo labels identifying a particular anatomical object in the one or more training medical images and 2) a distribution of the ground truth labels identifying the particular anatomical object in the one or more training medical images. The trained machine learning based model is fine-tuned for performing the medical imaging analysis task based on the filtered pseudo labels. In one embodiment, the filtering comprises determining a feature representation of each of the generated pseudo labels using a feature extractor model of the machine learning based model. A distance between a) the feature representation of each of the generated pseudo labels identifying the particular anatomical object in the one or more training medical images and b) the distribution of the ground truth labels identifying the particular anatomical object in the one or more training medical images is determined. The generated pseudo labels are filtered based on a comparison between the distances and a threshold. In one embodiment, the generating, the filtering, and the fine-tuning are repeated for a plurality of iterations.

In one embodiment, the trained machine learning based model is fine-tuned to maximize an overlap between a predicted location of the one or more anatomical objects and a location defined in the ground truth labels. In one embodiment, the trained machine learning based model is fine-tuned to maximize an overlap between a predicted location of unlabeled anatomical objects and a location defined in the pseudo labels for the unlabeled anatomical objects.

These and other advantages of the invention will be apparent to those of ordinary skill in the art by reference to the following detailed description and the accompanying drawings.

BRIEF DESCRIPTION OF THE DRAWINGS

FIG. 3 shows a method for training a machine learning based model for performing a medical imaging analysis task, in accordance with one or more embodiments;

FIG. 5 shows pseudocode 500 for implementing the steps of method 300 of FIG. 3, in accordance with one or more embodiments;

FIG. 8 shows a table summarizing public datasets used for experimental validation of one or more embodiments;

FIG. 9 shows a table summarizing the private datasets used for experimental validation of one or more embodiments;

FIG. 10 shows a table of segmentation performance for the experimental validation using the public datasets according to one or more embodiments;

FIGS. 11-13 show tables of segmentation performance for the experimental validation using the private datasets according to one or more embodiments;

FIG. 19 shows a table of Dice scores and ASD;

DETAILED DESCRIPTION

The present invention generally relates to methods and systems for learning from partially labeled datasets for medical imaging analysis. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Further, reference herein to pixels of an image may refer equally to voxels of an image and vice versa.

Embodiments described herein provide for training a single unified machine learning based model for performing multi-organ segmentation (or any other medical imaging analysis task) using partially labeled datasets. Such partially labeled datasets comprise a plurality of individual datasets each annotated to identify a respective organ of interest. A two-stage framework for training the unified machine learning based model is provided, termed the COSST framework, which effectively and efficiently integrates comprehensive supervision signals with self-training. During the first stage, the unified model is initially trained using ground truth labels. During the second stage, the trained unified model is fine-tuned by iteratively incorporating pseudo labels via self-training. Advantageously, embodiments described herein were experimentally found to have superior performance on various segmentation tasks and with different training data sizes over conventional approaches.

Figure 1:
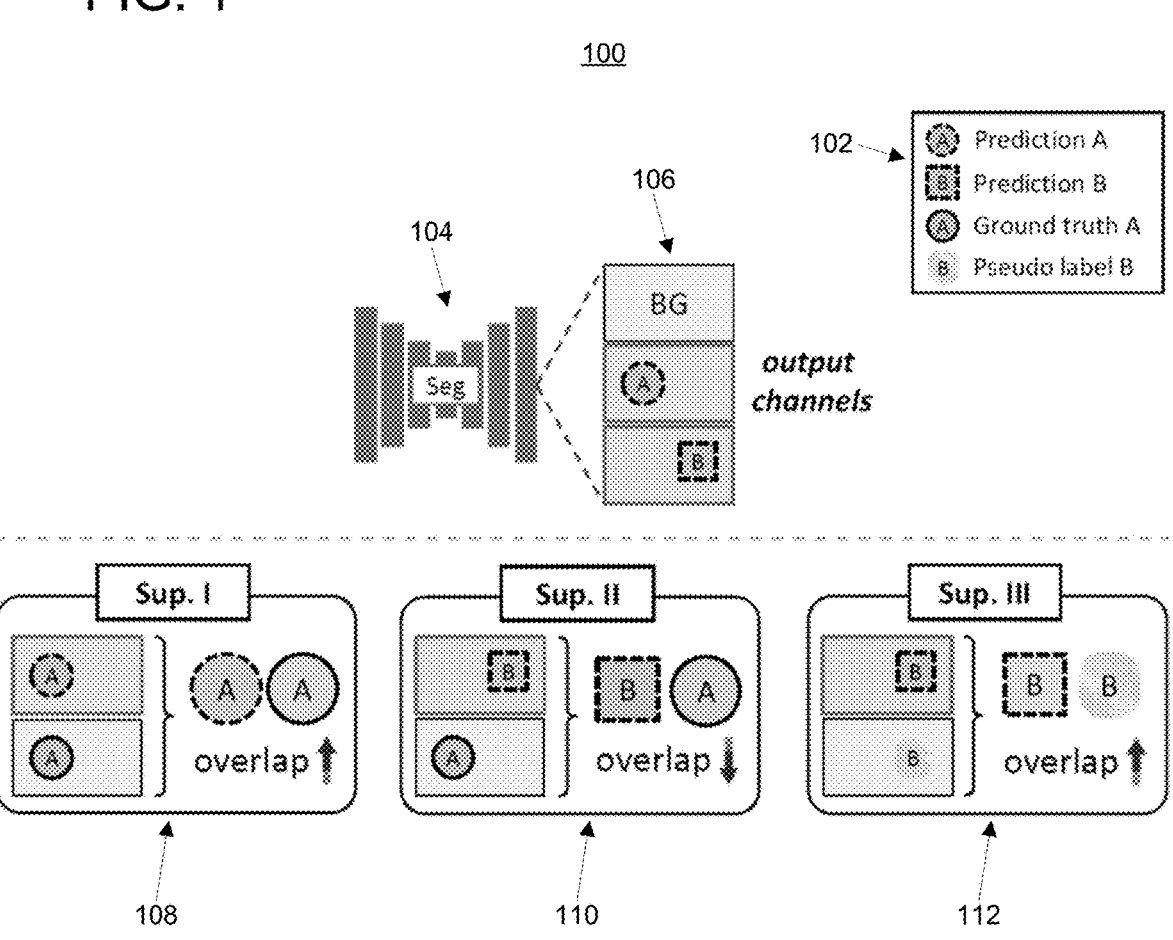
FIG. 1 shows a framework for training a machine learning based segmentation model using three types of supervision signals, in accordance with one or more embodiments.

FIG. 1 shows a framework 100 for training a machine learning based segmentation model using three types of supervision signals, denoted as Sup. I, Sup. II, and Sup. III, in accordance with one or more embodiments. Elements of framework 100 are defined in legend 102. In framework 100, machine learning based segmentation model 104 is trained using two partially labeled datasets: Dataset A (labeled with organ A) and Dataset B (labeled with organ B). Only Dataset A is labeled with ground truth labels. Dataset B is labeled with pseudo labels. Given Dataset A and Dataset B, segmentation model 104 generates output 106 comprising three channels: background (BG), Prediction A, and Prediction B. Given an input image from Dataset A, segmentation network 104 is trained according to Sup. I, Sup. II, and Sup. III.

As shown in block 108, Sup. I aims to maximize the overlap between the prediction of the labeled organ (organ A) and the corresponding ground truth labels. Sup. I utilizes the available ground truth labels for supervised learning.

As shown in block 110, Sup. II aims to minimize the overlap between the prediction of the unlabeled organ (organ B) and the ground truth labels of the labeled organ (organ A). This is because different organs must be mutually exclusive. In other words, each foreground voxel must be classified as either organ A or organ B in framework 100. The mutual exclusiveness can thus be used as a constraint to regularize the predictions of unlabeled organs based on the availability of labeled organs.

As shown in block 112, Sup. III aims to maximize the overlap between the prediction and the pseudo labels for the unlabeled organ (organ B). Compared to Sup. II, where the prediction of the unlabeled organ is constrained to where it cannot overlap, Sup. III imposes a stronger supervision by guiding the prediction to where it should overlap (i.e., to the pseudo labels). Such pseudo labels can be generated by, e.g., machine learning based models trained on individual partially labeled datasets.

Sup. I is applied to the labeled organs whereas Sup. II and Sup. III are applied to the unlabeled organs. Additionally, Sup. I and Sup. II are derived from ground truth labels, whereas Sup. III is derived from pseudo labels. Compared to Sup. III, which can be noisy due to unreliable pseudo labels, Sup. I and Sup. II are noise-free throughout the training process. Accordingly, in accordance with embodiments described herein, segmentation model 104 is initially trained during a first training stage according to Sup. I and Sup. II and fine-tuned during a second training stage according to Sup. III.

Figure 2:
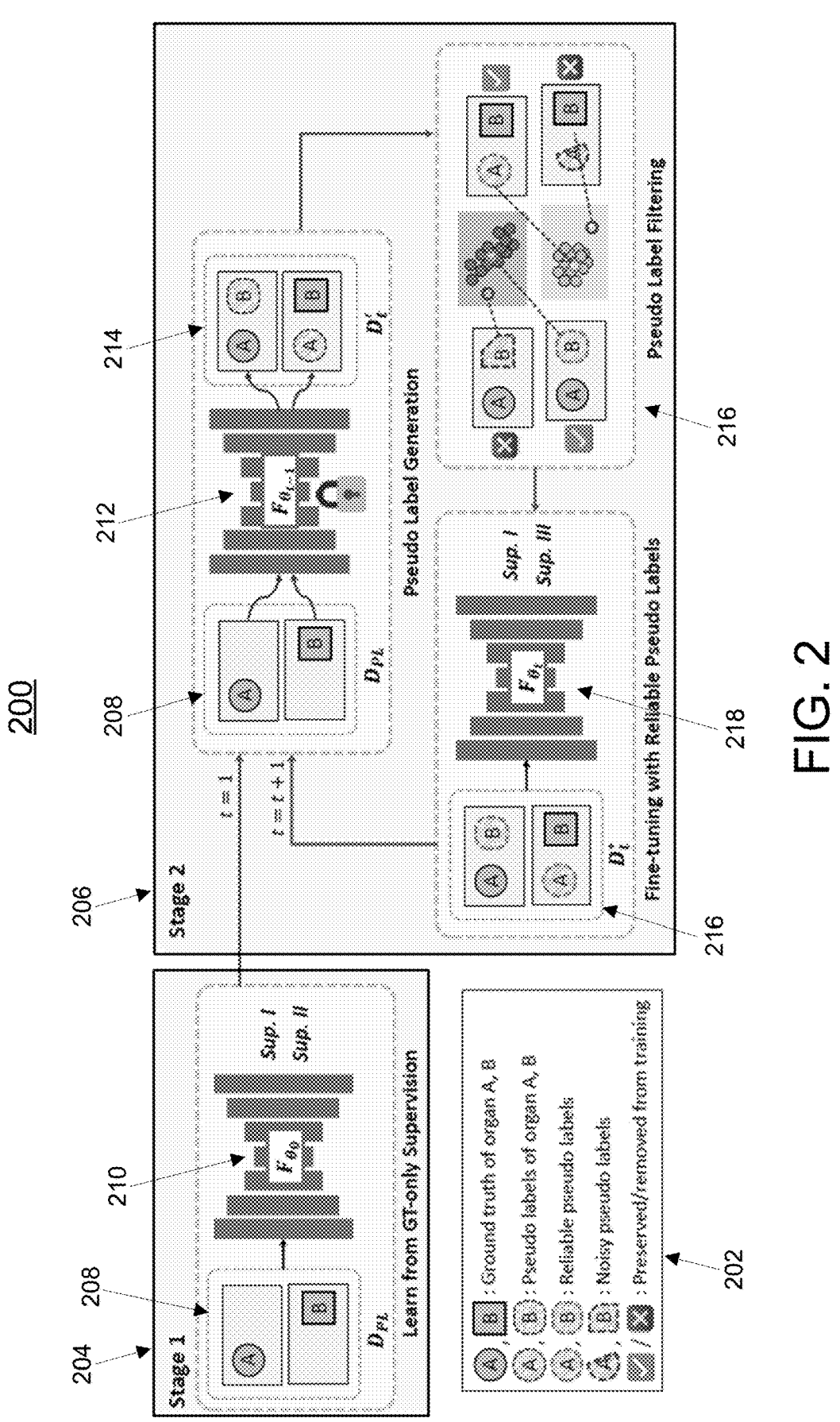
FIG. 2 shows a framework 200 for training a machine learning based model for performing a medical imaging analysis task, in accordance with one or more embodiments.

FIG. 2 shows a framework 200 for training a machine learning based model for performing a medical imaging analysis task, in accordance with one or more embodiments. Elements of framework 200 are defined in legend 202. FIG. 3 shows a method 300 for training a machine learning based model for performing a medical imaging analysis task, in accordance with one or more embodiments. The steps and/or sub-steps of method 300 of FIG. 3 may be performed using one or more suitable computing devices (e.g., computer 2600 of FIG. 26). FIG. 2 and FIG. 3 will be described together.

As shown in framework 200 of FIG. 2, a two-stage approach is proposed. In stage 1 204, a machine learning based model is trained using ground truth-based supervisions (according to Sup. I and Sup. II). In stage 2 206, the machine learning based model is iteratively fine-tuned using pseudo labels via self-learning. The steps of framework 200 of FIG. 2 and method 300 of FIG. 3 are performed during an offline or training stage for training the machine learning based model for performing the medical imaging analysis task. Once trained, the trained machine learning based model is applied during an online or inference stage, e.g., to perform the steps of method 700 of FIG. 7.

At step 302 of FIG. 3, one or more training medical images and ground truth labels identifying one or more anatomical objects in the one or more training medical images are received. In one embodiment, the one or more training medical images and the ground truth labels are part of a partially labeled dataset. In this embodiment, each of the one or more training medical images is respectively labeled with the ground truth labels to identify only one of the one or more anatomical objects. Formally, consider N partially labeled datasets $\mathcal{D}_{PL} = \{\mathcal{D}_1, \mathcal{D}_2, \ldots, \mathcal{D}_N\}$, which are respectively labeled with ground truth labels for anatomical objects $C_1, C_2, \ldots, C_N$. In one example, as shown in framework 200 of FIG. 2, the one or more training medical images and the ground truth labels are training medical images 208 with ground truth labels for organs A and B.

The one or more training medical images depict the one or more anatomical objects. The one or more anatomical objects may comprise organs, bones, vessels, tumors or other abnormalities, or any other anatomical object of interest of a patient. The one or more training medical images are labeled or annotated with the ground truth labels to identify the one or more anatomical objects. The ground truth labels may be pixel-wise (or voxel-wise) labels, where each pixel in the one or more training medical images is identified as depicting or not depicting the one or more anatomical objects. The one or more training medical images may be of any suitable modality, such as, e.g., CT, MRI (magnetic resonance imaging), US (ultrasound), x-ray, or any other medical imaging modality or combinations of medical imaging modalities. The one or more training medical images may comprise 2D (two dimensional) images and/or 3D (three dimensional) volumes.

Figure 26:
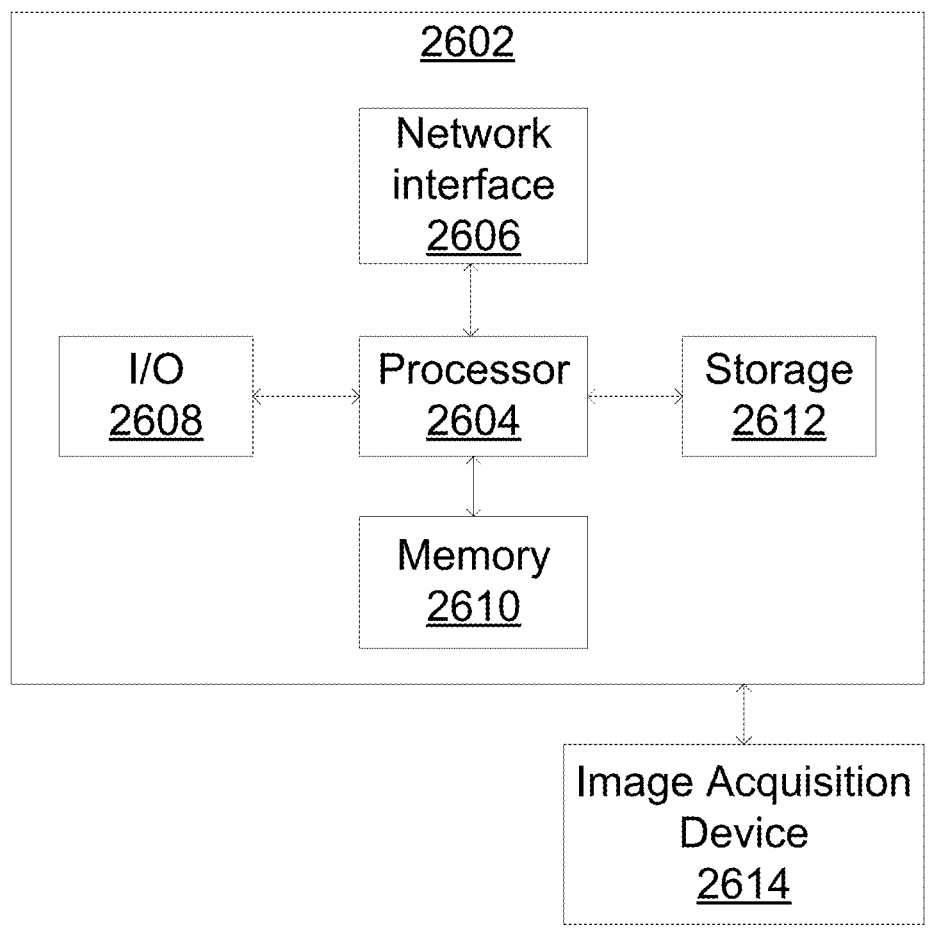
FIG. 26 shows a high-level block diagram of a computer that may be used to implement one or more embodiments.

The one or more training medical images and the ground truth labels may be received, for example, by directly receiving the one or more training medical images from an image acquisition device (e.g., image acquisition device 2614 of FIG. 26) as the images are acquired, by loading the one or more training medical images and the ground truth labels from a storage or memory of a computer system (e.g., memory 2610 or storage 2612 of computer 2602 of FIG. 26), or by receiving the one or more training medical images and the ground truth labels from a remote computer system (e.g., computer 2602 of FIG. 26). Such a computer system or remote computer system may comprise one or more patient databases, such as, e.g., an EHR (electronic health record), EMR (electronic medical record), PHR (personal health record), HIS (health information system), RIS (radiology information system), PACS (picture archiving and communication system), LIMS (laboratory information management system), or any other suitable database or system.

At step 304 of FIG. 3, a machine learning based model is trained for performing a medical imaging analysis task based on the one or more training medical images and the ground truth labels. In one example, as shown in framework 200 of FIG. 2, during stage 1 204, machine learning based model $F_{\theta 0}$ 210 is trained for performing a medical imaging analysis task based on training data 208 comprising training medical images labeled with ground truth labels for organs A and B. In one embodiment, the medical imaging analysis task is segmentation. However, the medical imaging analysis task may be any other suitable medical imaging analysis task, such as, e.g., detection, classification, quantification, etc.

The machine learning based model may be any suitable machine learning based model for performing the medical imaging analysis task. The machine learning based model receives as input the one or more training medical images and generates as output results of the medical imaging analysis task. The results of the medical imaging analysis task are then compared with the ground truth labels and the weights of the machine learning based model are updated to train the machine learning based model via supervised learning. The machine learning based model may be based on neural networks with multiple blocks of convolutional layers and/or attention layers to capture the high-level and low-level features from the medical images to support the medical imaging analysis task.

The machine learning based model is trained according to supervision signals derived only from the ground truth annotations (i.e., according to Sup. I and Sup. II). In accordance with Sup. I, for labelled anatomical objects, the machine learning based model is trained with supervised learning using the ground truth labels. In this way, the machine learning based model is trained to maximize the overlap between the predicted location of the anatomical object and the location defined in the ground truth label for a training medical image. In accordance with Sup. II, for unlabeled anatomical objects, the machine learning based model is trained with supervised learning to not overlap the annotated anatomical objects. In this way, the machine learning based model is trained to minimize the predicted location of an unlabeled anatomical object and the location defined in the ground truth label for a training medical image.

One challenge in training the machine learning based model according to Sup. I and Sup. II is that there are typically certain labels absent in partially labeled data, making many traditional segmentation loss functions inapplicable. In accordance with one or more embodiments, for the one or more anatomical objects (labeled according to the ground truth labels), unlabeled anatomical objects are treated as background by merging the output channels of the original background channel and all unlabeled anatomical objects into a new background channel. The merging may be performed by taking the sum of the probabilities. Given image x, the original model prediction $\tilde{y}=F(x; \theta)$ is thus transformed to a new prediction $\tilde{y}_r$, which only has the output channels of the new background and the labeled anatomical objects, allowing for many traditional segmentation losses to be directly applied. For unlabeled anatomical objects, a binary mask M is created by taking the union of all labeled anatomical objects. All output channels of unlabeled anatomical objects are then regularized by minimizing the overlap between the prediction on each channel and the binary mask. Let y be the ground truth label, $C_u$ be the number of unlabeled anatomical objects, and L be a segmentation loss (e.g., the Dice loss). The overall loss function for training the machine learning based model can be defined as in Equation (1):

$$\theta_0 = \operatorname*{argmin}_{\theta} L(\tilde{y}_t, y) - \sum_{u \in C_u} L(\widetilde{y_u}, M) \tag{1}$$

Steps 306, 308, and 310 of FIG. 3 are iteratively repeated for one or more iterations for fine-tuning the trained machine learning based model for performing the medical imaging analysis task. In one example, as shown in framework 200 of FIG. 2, the steps of stage 2 206 are iteratively repeated for t iterations for fine-tuning machine learning based model $F_{\theta 0}$ 210. The fine-tuning process is iteratively repeated until, for example, the performance of the machine learning based model plateaus on a validation dataset and/or for a predetermined number of iterations. It should be understood that while machine learning based models $F_{\theta 0}$ 210, $F_{\theta r-1}$ 212, and $F_{\theta r}$ 218 are separately shown for illustrative purposes, machine learning based models $F_{\theta 0}$ 210, $F_{\theta r-1}$ 212, and $F_{\theta r}$ 218 are the same model with different weights (which are updated at each iteration t).

At step 306 of FIG. 3, pseudo labels identifying the one or more anatomical objects in the one or more training medical images are generated using the trained machine learning based model (as trained at step 304 of FIG. 3).

Pseudo labels refer to predicted labels, for example, using one or more machine learning based models. In one example, as shown in framework 200 of FIG. 2, during stage 2 206, pseudo labels 214 are generated by trained machine learning based model $F_{\theta r-1}$ 212 (trained during stage 1 204) from training images 208.

The trained machine learning based model receives as input the one or more training medical images of partially labeled datasets $\mathcal{D}_{PL}$ and generates as output predicted pseudo labels of the one or more training medical images. The predicted pseudo labels form a pseudo multi-anatomical object dataset $\mathcal{D}'_r$. The quality of pseudo labels is highly dependent on the performance of the trained machine learning based model. Accordingly, self-training is utilized to optimize the usage of the pseudo labels. Specifically, at iterations $t \in \{1,2,3, \ldots \}$, machine learning based model $F_{\theta r-1}$ (i.e., the machine learning based model from the immediately prior iteration) is utilized to generate the pseudo labels for unlabeled anatomical objects. The prediction $\tilde{y}=F(x; \theta_{r-1})$ are obtained as pseudo labels and the pseudo labels of unlabeled anatomical objects are merged to y, with the original ground truth labels retained. During the merging, the ground truth labels have higher priority than the pseudo labels when there are conflicting labels. As a result, a pseudo multi-anatomical object dataset $\mathcal{D}'_r$ is obtained where each training data is fully annotated by the merged labels. The initial machine learning based model $F_{\theta 0}$ 210 is fine-tuned on the pseudo multi-anatomical object dataset $\mathcal{D}'_r$. The loss function for fine-tuning the machine learning based model can be defined as in Equation (2):

$$\theta_t = \operatorname*{argmin}_{\theta} L(\tilde{y}_t, y'_t; \theta_0) \tag{2}$$

where $y'_t \in \mathcal{D}'_r$. Self-training offers an efficient way to train machine learning based model $F_{\theta 0}$ (trained according to Sup. I and Sup. II) on the most updated pseudo labels (according to Sup. III).

At step 308 of FIG. 3, optionally, the generated pseudo labels are filtered based on a comparison between 1) each of the generated pseudo labels identifying a particular anatomical object in the one or more training medical images and 2) a distribution of the ground truth labels identifying the particular anatomical object in the one or more training medical images. In one example, as shown in framework 200 of FIG. 2, pseudo labels 214 are filtered at block 216.

The quality of the pseudo labels is important in self-training, as unreliable pseudo labels may lead to confirmation bias and potential performance degradation. To better exploit the pseudo labels during self-training, a pseudo label assessment and filtering strategy is provided. For each anatomical object, ground truth labels are available in at least one of the one or more training medical images. Therefore, given the distribution of the available ground truth labels, the quality of a pseudo label can be assessed via outlier detection in the latent space: if a pseudo label is a clear outlier deviating from the distribution of the ground truth labels, it is very likely to be a noisy label.

Figure 4:
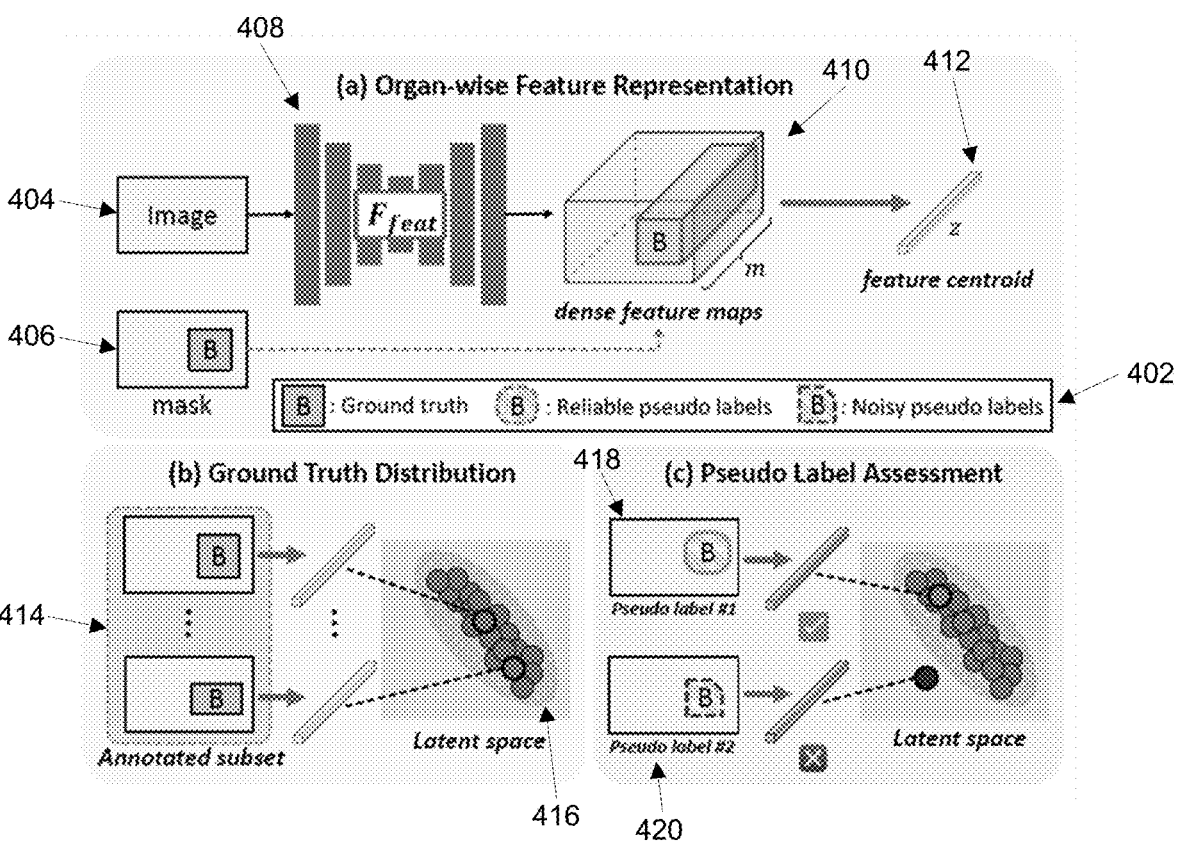
FIG. 4 shows a framework for filtering pseudo labels, in accordance with one or more embodiments.

FIG. 4 shows a framework 400 for filtering pseudo labels, in accordance with one or more embodiments. Elements of framework 400 are defined in legend 402. Each anatomical object (both labeled and unlabeled) in each of the one or more training medical images is represented as a feature vector using the merged label y'. Given a network input of $x \in \mathbb{R}^{ch \times h \times w \times d}$ with ch channels, h height, w width, and d depth, a machine learning based segmentation model F can be decomposed as (1) a dense feature extractor $F_{feat}$: $\mathbb{R}^{ch \times h \times w \times d} \to \mathbb{R}$ m×h×w×d and (2) a subsequent voxel-wise classifier $F_{cls}$: $\mathbb{R}^{m \times h \times w \times d} \to [0,1]^{(1+C_{PL}) \times h \times w \times d}$ that projects the m dimensional features into class predictions. Accordingly, for the i-th training medical image x; 404, the voxel-wise feature representation 410 is first calculated using the dense feature extractor $\mathcal{F}_{feat}$ 408 (e.g., decomposed from machine learning based model 210 of FIG. 2), where the feature representation 410 of the j-th voxel is expressed as $\mathcal{F}_{feat}(x_i)^j$. For the k-th anatomical object, the anatomical object-wise feature representation $z^{(i,k)} \in \mathbb{R}^m$ is obtained by computing the feature centroid 412 for all voxels belonging to the mask $y'^{(k)}$ 406 as defined in Equation (3):

$$z^{(i,k)} = \frac{\sum_J \mathcal{F}_{feat}(x_i)^j * \mathbb{1}\left(y'^{(j,k)} == 1\right)}{\sum_J \mathbb{1}\left(y'^{(j,k)} == 1\right)} \quad (3)$$

where $\mathbb{1}$ is the indicator function. PCA (principal component analysis) is used to reduce the dimension of z from m to 2, which is empirically more effective and computationally more efficient. Let n be the number of training medical images with the k-th anatomical object labeled, thereby forming annotated dataset 414. The ground truth distribution 416 for the k-th anatomical object can thus be expressed as: $z^k = \{z^{i,k}, \ldots, z^{i+1,k}\}$.

Given the ground truth distribution $z^k$, each pseudo label is assessed to determined whether it is an outlier. In one embodiment, the Mahalanobis distance is used to compare each pseudo label with its ground truth distribution $z^k$. Other distances may also be employed. The Mahalanobis distance considers the intra-class relationship by taking into account the covariance matrix. The Mahalanobis distance d between the pseudo label $\bar{z}^k$ and the ground truth distribution $z^k$ can be expressed as: $d^2(\bar{z}^k, \mu, C) = (\bar{z}^k - \mu)^T \cdot C^{-1} \cdot (\bar{z}^k - \mu)$, where $\mu$ and C represent the mean feature vector and covariance matrix of $z^k$, respectively. To detect the outlier, a threshold t is defined for the Mahalanobis distance and a pseudo label is considered unreliable and thus filtered if $d(\bar{z}^k, \mu, C) > \tau$. For example, as shown in framework 400 of FIG. 4, pseudo label 418 satisfies threshold t and is therefore considered to be a reliable pseudo label while pseudo label 420 does not satisfy threshold $\tau$ and is therefore considered to be a noisy (unreliable) pseudo label.

The detected unreliable pseudo labels may cause performance degradation and thus should be denoised or removed before training. Accordingly, the pseudo labels are filtered on the image level. Specifically, the training medical images with unreliable pseudo labels are removed from the pseudo multi-anatomical object dataset $\mathcal{D}'_t$, resulting in a filtered dataset $$\mathcal{D}^*_t.$$

Returning back to FIG. 3, at step 310, the trained machine learning based model is fine-tuned for performing the medical imaging analysis task based on the one or more training medical images, the ground truth labels, and the generated pseudo labels. In one example, as shown in framework 200 of FIG. 2, machine learning based model $F_{\theta_t}$ 218 is fine-tuned based on filtered dataset $$\mathcal{D}^*_t.$$

By incorporating the pseudo label filtering to self-training, the overall loss function of self-training at iteration t from Equation (2) is replaced with Equation (4):

$$\theta_t = \operatorname*{argmin}_{\theta} L(\tilde{y}, y^*_t; \theta_0) \quad (4)$$

where $$y^*_t \in \mathcal{D}^*_t.$$

Both the labeled (Sup. I) and the unlabeled (Sup. II) anatomical objects are optimized jointly in Equation (4). As such, the trained machine learning based model is fine-tuned according to Sup. I to maximize an overlap between a predicted location of the one or more anatomical objects and a location defined in the ground truth labels and according to Sup. III to maximize an overlap between a predicted location of unlabeled anatomical objects and a location defined in the pseudo labels for the unlabeled anatomical objects. This approach also mitigates the information loss caused by image-level filtering (i.e., the labeled anatomical objects in the images that were filtered out are excluded from training) by fine-tuning on the initial machine learning based model, where all labeled anatomical objects have been used as ground truth based supervision signals in stage 1.

At step 312, the fine-tuned machine learning based model is output. For example, the fine-tuned machine learning based model can be output by storing the fine-tuned machine learning based model on a memory or storage of a computer system (e.g., memory 2610 or storage 2612 of computer 2602 of FIG. 26) or by transmitting the fine-tuned machine learning based model to a remote computer system (e.g., computer 2602 of FIG. 26).

FIG. 5 shows pseudocode 500 for implementing the steps of method 300 of FIG. 3, in accordance with one or more embodiments.

Figure 6:
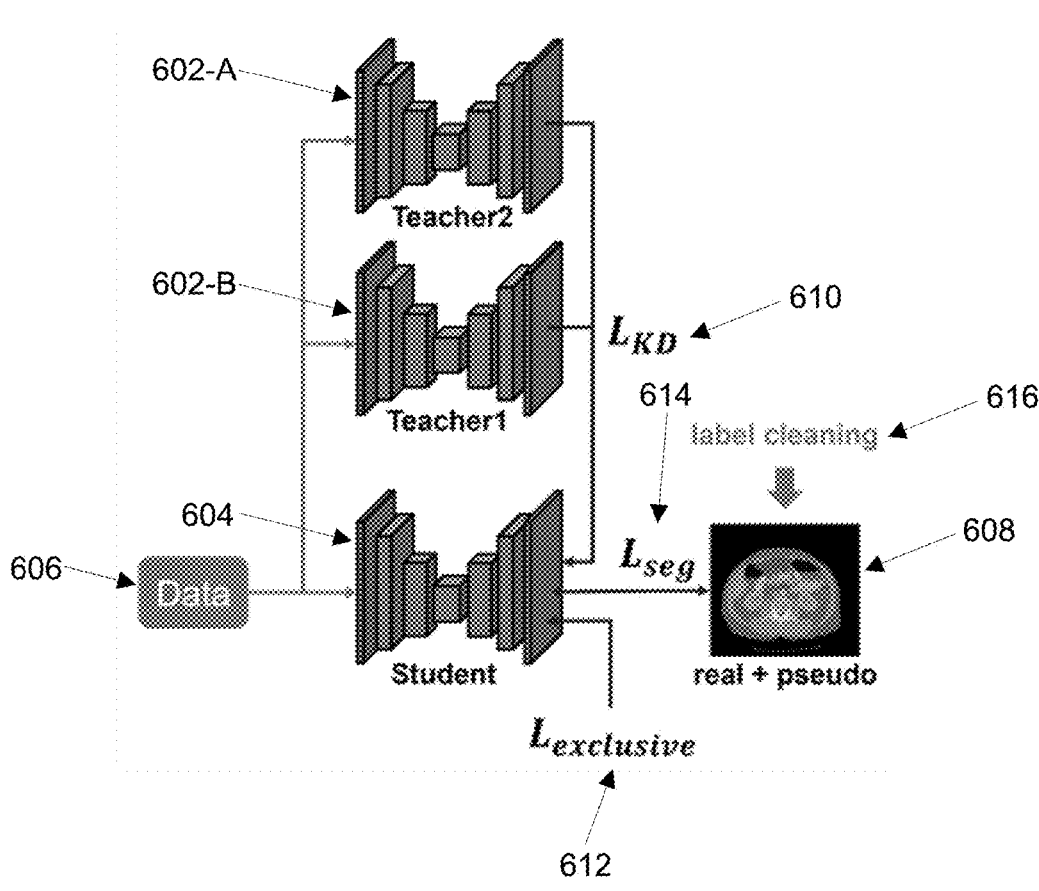
FIG. 6 shows a framework 600 for training a machine learning based model for performing a medical imaging analysis task using pseudo label training and knowledge distillation using a student-teacher approach, in accordance with one or more embodiments.

In one embodiment, instead of the two-stage approach described in framework 200 of FIG. 2 and method 300 of FIG. 3, learning from partially labeled datasets may be performed using a student-teacher approach. FIG. 6 shows a framework 600 for training a machine learning based model for performing a medical imaging analysis task using pseudo label training and knowledge distillation using a student-teacher approach, in accordance with one or more embodiments.

Given training data 606 comprising N partially labeled datasets $\mathcal{D}_{PL} = \{\mathcal{D}_1, \mathcal{D}_2, \ldots, \mathcal{D}_N\}$, which are respectively labeled with ground truth labels for anatomical objects $C_1$, $C_2, \ldots, C_N$. To generate pseudo labels, separate initial machine learning based models 602-A and 602-B (collectively referred to as models 602) are first trained with $\mathcal{D}_{PL}$ via supervised learning (similar to step 304 of FIG. 3), resulting in N models denoted as $M = \{M_1, M_2, \ldots, M_N\}$. Once trained, the trained models M are applied to each dataset $\mathcal{D}_{PL}$ to generate pseudo labels (similar to step 306 of FIG. 3). For example, the pseudo labels of dataset $\mathcal{D}_1$ can be obtained by $M_2(\mathcal{D}_1) \cup M_3(\mathcal{D}_1) \cup \ldots \cup M_N(\mathcal{D}_1)$. The ground truth labels for the foreground voxels are prioritized when both pseudo labels and ground truth labels exist for a particular voxel, since there is more confidence in the quality of the ground truth labels.

Once the pseudo labels are generated on all partially labeled datasets $\mathcal{D}_{PL}$, a machine learning based model 604 is trained via supervised learning. In this setting, the labeled and unlabeled anatomical objects 608 are supervised separately by the ground truth labels and the pseudo labels, respectively, via segmentation loss function $L_{seg}$ 614. Although the pseudo labels may be noisy, they can provide valuable supervision signals for the unlabeled anatomical objects. The output channels are further regularized by an exclusive loss function $L_{exclusive}$ 612. With the pseudo label training and the exclusive loss $L_{exclusive}$ 612, the machine learning based model 604 can be trained with awareness of where the unlabeled anatomical objects should and should not overlap. Furthermore, the quality of the pseudo labels may be improved via label cleaning 616. Label cleaning 616 can be performed in either subject-wise or voxel-wise. In subject-wise label cleaning, the 2D visualization of the pseudo labels are created and poor-quality pseudo labels are manually filtered out. In vox-wise label cleaning, well known label cleaning methods may be applied (e.g., clean-lab).

In one embodiment knowledge distillation may additionally be performed to transfer the knowledge from a complex teacher model to a shallow student model. For instance, consider the trained models M 602 as the teacher models and the machine learning based model 604 as the student model. The output activations of teacher models 602 are distilled to a single student model 604. In the example in framework 600 of FIG. 6, each teacher model 602 was trained to segment separate anatomical objects while student model 604 aims to segment all available anatomical objects. Thus, teacher models 602 and student model 604 have different number of output channels. To overcome this issue, the knowledge from each teacher model 602 is distilled to student model 604 via knowledge distillation loss $L_{KD}$ 610. Each time, the knowledge distillation loss $L_{KD}$ 610 is only computed for the anatomical objects labeled with ground truth labels in the current teacher model 602. In implementation, teacher models 602 can be much more complex than student model 604. The stronger the teacher model 602, the better the knowledge that can be distilled to the student model 604. In summary, knowledge distillation from multiple teachers 602 provide soft labels as supervision to complement the pseudo labels from pseudo label training. Both pseudo label training and knowledge distillation from multiple teachers 602 are flexible and scalable.

Figure 7:
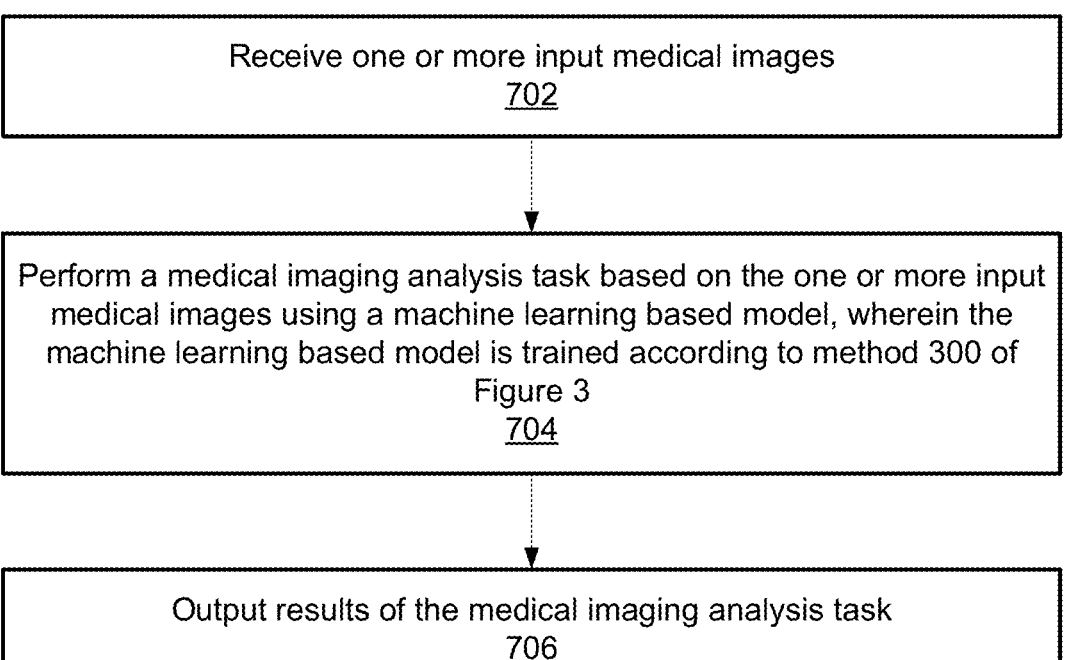
FIG. 7 shows a method for performing a medical imaging analysis task using a trained machine learning based model, in accordance with one or more embodiments.

FIG. 7 shows a method 700 for performing a medical imaging analysis task using a trained machine learning based model, in accordance with one or more embodiments. The steps and/or sub-steps of method 700 of FIG. 7 may be performed using one or more suitable computing devices (e.g., computer 2600 of FIG. 26). The steps of method 700 of FIG. 7 are performed during an online or inference stage using a trained machine learning based model.

At step 702 of FIG. 7, one or more input medical images are received. The one or more input medical images depict one or more anatomical objects, such as, e.g., organs, bones, vessels, tumors or other abnormalities, or any other anatomical object of interest of a patient. The one or more input medical images may be of any suitable modality, such as, e.g., CT, MRI, US, x-ray, or any other medical imaging modality or combinations of medical imaging modalities. The one or more input medical images may comprise 2D images and/or 3D volumes.

The one or more input medical images may be received, for example, by directly receiving the one or more input medical images from an image acquisition device (e.g., image acquisition device 2614 of FIG. 26) as the images are acquired, by loading the one or more input medical images from a storage or memory of a computer system (e.g., memory 2610 or storage 2612 of computer 2602 of FIG. 26), or by receiving the one or more input medical images from a remote computer system (e.g., computer 2602 of FIG. 26). Such a computer system or remote computer system may comprise one or more patient databases.

At step 704 of FIG. 7, a medical imaging analysis task is performed based on the one or more input medical images using a machine learning based model. In one embodiment, the medical imaging analysis task is segmentation. However, the medical imaging analysis task may be any other suitable medical imaging analysis task, such as, e.g., detection, classification, quantification, etc. The machine learning based model may be any suitable machine learning based model for performing the medical imaging analysis task. The machine learning based model receives as input the one or more input medical images and generates as output results of the medical imaging analysis task. In one embodiment, the machine learning based model is trained according to framework 200 of FIG. 2 and/or method 300 of FIG. 3. In another embodiment, alternatively, the machine learning based model is trained according to framework 600 of FIG. 6.

At step 706 of FIG. 7, results of the medical imaging analysis task are output. For example, the results of the medical imaging analysis task can be output by displaying the results of the medical imaging analysis task on a display device of a computer system (e.g., I/O 2608 of computer 2602 of FIG. 26), storing the results of the medical imaging analysis task on a memory or storage of a computer system (e.g., memory 2610 or storage 2612 of computer 2602 of FIG. 26), or by transmitting the results of the medical imaging analysis task to a remote computer system (e.g., computer 2602 of FIG. 26).

The COSST framework, in accordance with one or more embodiments described with respect to framework 200 of FIG. 2 and method 300 of FIG. 3, was experimentally validated. The experimental validation was performed using public datasets and private datasets.

Public Datasets: In the experimental validation, four public, partially labeled CT datasets were used for training, including (1) the task03 liver dataset from Medical Segmentation Decathlon (MSD), (2) the task09 spleen dataset from MSD, (3) the task07 pancreas dataset from MSD, and (4) the KiTS19 (2019 Kidney and Kidney Tumor Segmentation challenge) dataset. The cancer label to the organ label for liver, pancreas and kidney datasets were merged. In addition, the binary kidney masks were manually divided into left and right kidneys through connected component analysis. In this task, the goal is to train a single unified segmentation model from the partially labeled datasets to segment all five organs, i.e., left kidney, right kidney, spleen, liver, and pancreas. This task will be referred to herein as task1. For evaluation, besides the held-out testing sets from the MSD and KiTS19 datasets, additional evaluation was performed on two external public CT datasets, i.e., BTCV (Beyond the Cranial Vault) and AMOS2022 (A Large-Scale Abdominal Multi-Organ Benchmark for Versatile Medical Image Segmentation Challenge 2022). This evaluation can be used to assess the model's generalizability to unseen CT datasets collected from different scanners and sites, which is common yet challenging in practice. To summarize, the testing set consists of a total number of 662 CT scans. FIG. 8 shows a table 800 summarizing the public datasets for task1. The column "#organs) refers to the number of organs that are related to the task.

Private Datasets: Experiments were also conducted on our private CT datasets for three partial-label segmentation tasks. These tasks aim to segment more diverse sets of organs from three body regions, i.e., bowel, pelvic and eye regions, which are referred to herein as task2, task3, and task4, respectively. Specifically, each task consists of two partially labeled CT datasets and each dataset may contain multiple annotated organs. The datasets were acquired from regular radiotherapy planning routine and the organs were annotated by a team of experienced specialists with an internal annotation tool. For each organ, a detailed annotation protocol was set up based on Radiation Therapy Oncology Group (RTOG) guidelines. A quality assessment was performed for each annotated dataset before further use. In contrast to the existing studies where single-organ datasets are mostly used, the private partially labeled datasets utilized in the experiments are mostly annotated with multiple organs, leading to a rarely studied yet more challenging experimental setting. FIG. 9 shows a table 900 summarizing the private datasets for tasks2-4, where L refers to left and R refers to rights.

The fully-annotated training sets of bowel datasets were obtained by having specialists additionally annotate the unlabeled organs on the partially labeled datasets. Thus, the bowel datasets were also used to (1) compare the model trained with partially labeled datasets against fully-annotated datasets (upper bound) and (2) comprehensively evaluate the quality of pseudo labels as later shown in our ablation study.

Implementation Details: For task1, nnU-Net was selected due to its demonstrated superior performance across a spectrum of MICCAI (medical imaging computing and computer assisted interventions) segmentation challenges. The output layer of the network is activated by softmax and the number of output channels is set to CPL+1. For preprocessing, all CT scans were adjusted to the RAI (radiology affiliates imaging) orientation, resampled to 1.5×1.5×3.0 mm, clipped to [−1024, 1024] Hounsfield Units (HU), and rescaled to [0, 1]. The wide window was used for intensity clipping to ensure fair contrast for different types of organs such as soft tissues and bones. For all compared methods and the stage 1 of COSST, we use the same hyperparameters configured by nnU-Net for training, including a total number of 1000 training epochs, an initial learning rate of 0.01, an optimizer of the stochastic gradient descent (SGD) algorithm with a Nesterov momentum ($\mu$=0.99), and a learning rate scheduler of polynomial decay policy. The patch size is configured as 160×192×64 by the nnU-Net. The model checkpoints with the best performance on the validation set are selected for final evaluation. For the stage 2 of COSST, i.e., fine-tuning with self-training, the maximum number of epochs was set as 200 and the initial learning rate as 0.0001. The other hyperparameters and the model selection criteria are kept the same as the stage 1.

For task2-4, the classical 3D U-Net was adopted as the backbone architecture and the same preprocessing procedures and hyperparameters (learning rate, optimizer, and epochs) was used as in task1. During training, 3D patches were randomly extracted with a fixed size of 128×128×128 with the center being a foreground or background voxel using a ratio of 2:1. To achieve optimal performance for all compared methods, a variety of augmentation techniques were applied on-the-fly including rotation, scaling, Gaussian blur, Gaussian noise, brightness, contrast, low resolution simulation and gamma correction. The sum of Dice loss and cross-entropy loss was used as the segmentation loss. During inference, the sliding window inference was used with a window step size equal to half of the patch size and the overlapping windows are merged using Gaussian weighting. For all segmentation tasks, the threshold for Mahalanobis distance T was empirically set as $\chi^2(2,0.999)$, i.e., the 99.9% quantile of the chi-squared distribution with a degree of freedom of 2. All experiments were implemented in PyTorch v1.10 and MONAI v0.8 with a single NVIDIA V100 16 GB GPU.

Evaluation Metrics: Dice Similarity Coefficient (DSC), average symmetric surface distance (ASD), and 95th Hausdorff distance (HD95) were used to evaluate the segmentation performance. DSC computes the overlapping between the predicted mask and ground truth. ASD evaluates the quality of segmentation boundaries by computing the average of all distances between the predicted mask and the ground truth boundary. HD95 is the 95th percentile of the maximum distances between the boundary points in the prediction and the ground truth, which suppresses the impact of outlier voxels in the prediction. In our experiments, all the validation and testing sets (except for the external testing datasets for task1) are also partially labeled datasets. For these datasets, the average metrics for each organ are only computed based on the dataset where the organ is annotated. For the same reason, Wilcoxon signed-rank test used for statistical analysis is conducted on the metrics of individual organs for the held-out testing sets of MSD and KiTS19 in task1 and all testing sets in task2-4, and on the average metrics of all organs for BTCV and AMOS2022 testing sets.

Comparison With Conventional Methods: The proposed COSST approach was compared against seven conventional approaches that also address the partial-label segmentation problem. The compared methods are (1) individual networks trained on each partially labeled dataset (Multi-Nets), (2) two methods that utilize only the ground truth-based supervision: target adaptive loss and marginal and exclusive loss (denoted as TAL and ME), (3) three methods that employ pseudo label supervision: pseudo label training, Co-training of weight-averaged models, a multi-teacher single-student knowledge distillation framework that exploits soft pseudo labels (denoted as PLT, Co-training, and MS-KD), (4) DoD-Net: a state-of-the-art conditioned network. To ensure fair comparison, the same backbone architecture and training strategies were used for all compared methods.

In table 1000 of FIG. 10, the segmentation performance of the compared methods for the public datasets in task1 is shown. In table 1000, DSC is shown as a percentage where the higher is better, HD95 is shown in mm (millimeters) where lower is better, and ASD is shown in mm where lower is better. The symbols † and * represent p-value <0.5 and <0.1 using Wilcoson signed-rank test; otherwise, p-value >0.05. P represents held-out testing sets of MSD and KiTS19, F1 represents BTCV, and F2 represents AMOS2022. First, it is observed that it is more beneficial to learn a single unified model from partially labeled datasets than the baseline Multi-Nets, especially for the organs whose training set is small, e.g., spleen (N=20). For example, by comparing the Multi-Nets to the proposed COSST, we can observe that the average Dice score improves from 86.25% to 89.08%, the average HD95 improves from 16.85 to 5.36, and the average ASD improves from 3.38 to 1.16. By comparing the segmentation performance across three evaluated datasets, the segmentation performance of all compared methods decreases from the heldout testing set to the external datasets, e.g., the average Dice score of COSST drops from 92.13% to 87.76% and 87.37% for BTCV and AMOS2022, respectively. However, COSST was found to consistently yield more reliable segmentation results than other methods under the domain shift. For instance, by the comparing the COSST to the second best approach, it is shown that the segmentation results of COSST have much better boundary matching, i.e., 6.23 vs. 11.24 and 6.29 vs. 11.01 respectively for BTCV and AMOS2022. For ground truth-based supervision methods, it is observed that TAL and ME achieve comparable results in Dice scores but TAL slightly outperforms ME in HD95 and ASD. In addition, it is noted that the pseudo label-based methods such as PLT and Co-training achieve better segmentation performance than the non-pseudo label based methods, i.e., TAL and ME, demonstrating the importance of the pseudo label learning. Furthermore, comparing the pseudo label based methods (e.g., PLT) to the proposed COSST, it is observed that COSST not only achieves overall higher Dice scores, but also much better performance in distance-based metrics HD95 and ASD (ASD: 1.16 vs. 2.51, and HD95: 5.36 vs. 14.91), indicating the effectiveness of our strategy for pseudo label learning, i.e., pseudo label filtering with self-training. Overall, COSST achieves consistent superior segmentation performance than all compared methods on all three evaluated CT datasets, especially in the distance-based metrics HD95 and ASD.

Figure 14:
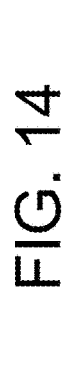
FIG. 14 shows images of a qualitative comparison between one or more embodiments and conventional methods of bowel datasets.
Figure 15:
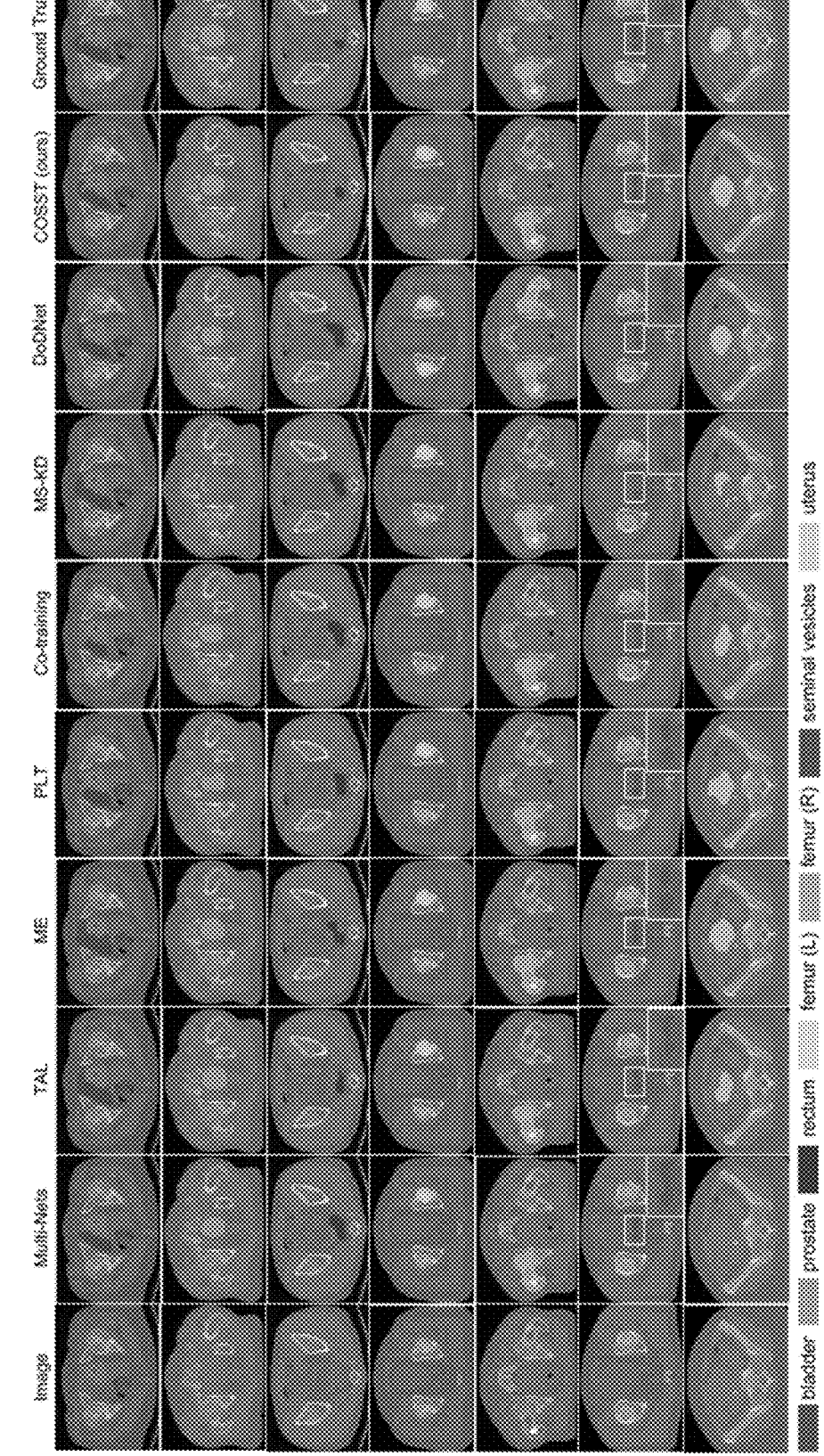
FIG. 15 shows images of a qualitative comparison between one or more embodiments and conventional methods of pelvic datasets.
Figure 16:
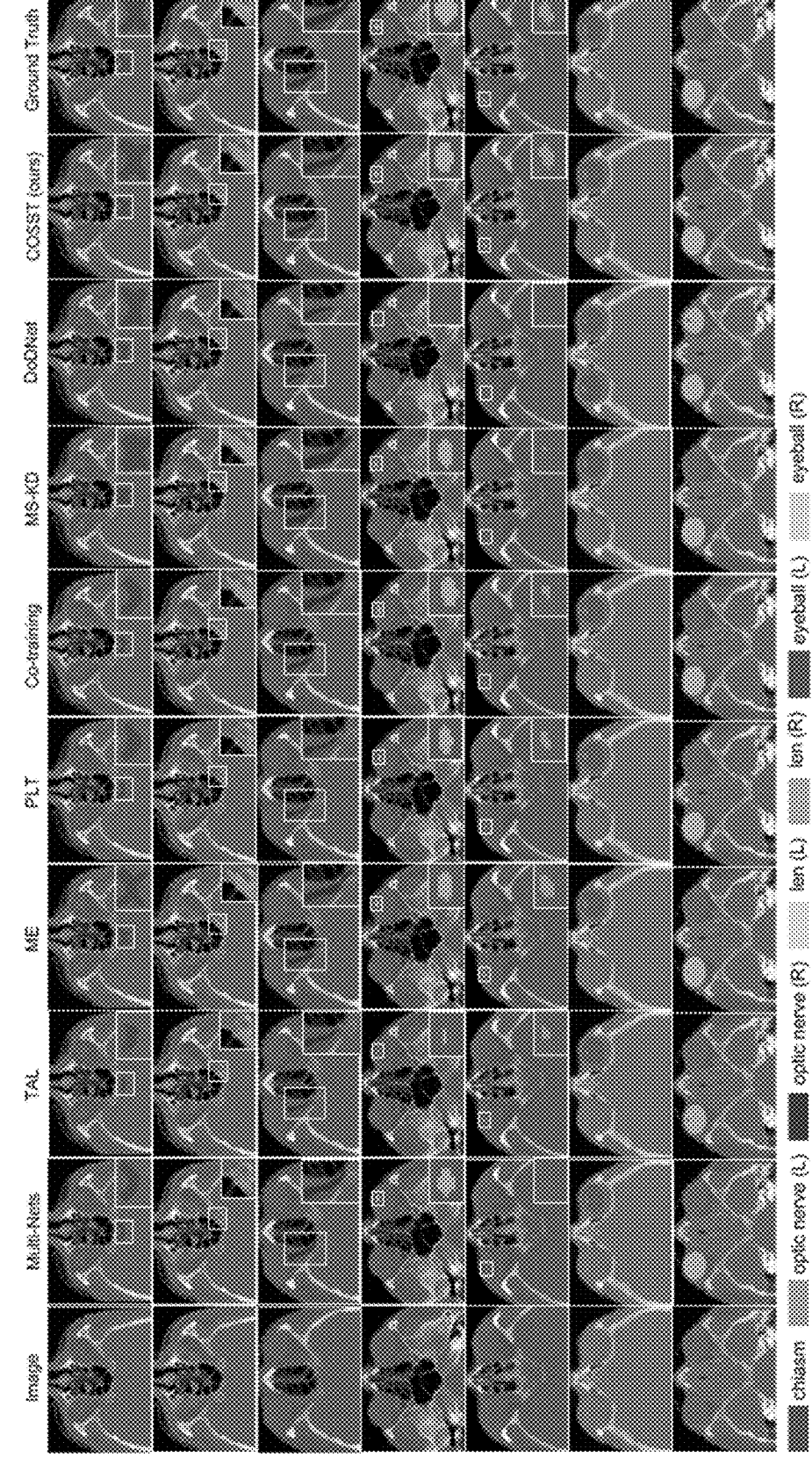
FIG. 16 shows images of a qualitative comparison between one or more embodiments and conventional methods of eye datasets.

Table 1100 of FIG. 11, table 1200 of FIG. 12, and table 1300 of FIG. 13 tabulate the segmentation performance on the private datasets for task2, task3, and task4, respectively. The results reveal that most partial-label segmentation approaches outperform the baseline Multi-Nets, demonstrating the benefits of training a single network on the union of partially labeled datasets. For the ground truth-based supervision methods, it is observed that ME consistently outperforms TAL on all three segmentation tasks. For the pseudo label-based methods, Co-training achieves consistent better performance than PLT. The performance of MS-KD does not appear competitive as it is even worse than the baseline Multi-Nets. The conditioned network DoDNet achieves suboptimal results in our experiments, especially for the small organs in bowel datasets, i.e., duodenum and rectum. However, it achieves superior performance on the gender-specific organs such as seminal vesicles and uterus in pelvic datasets (table 1200 of FIG. 12). In addition, it fails to distinguish the left and right labels for symmetric organs, such as femurs and optic nerves. Lastly, the proposed COSST achieves the highest overall segmentation performance among the competing partial-label segmentation methods on all three segmentation tasks (except the second best ASD on eye dataset). Furthermore, in table 1100 of FIG. 11, the results show that the performance achieved by COSST is comparable to the upper bound, i.e., the network trained with fully-annotated datasets. Especially, COSST achieves significant improvements on complex structures such as small bowel and large bowel. Images 1400 of FIG. 14, images 1500 of FIG. 15, and images 1600 of FIG. 16 show qualitative comparisons between the proposed COSST approach and conventional partial label segmentation methods on bowel datasets for task 2, pelvic datasets for task 3, and eye datasets for task4, respectively. Qualitatively, it is observed in images 1400, 1500, and 1600 that COSST provides more reasonable segmentation than other partial-label segmentation approaches on bowel datasets. In images 1400, the first (top) row through the fifth (bottom) row respectively show segmentation of the duodenum, the small bowel, the large bowel, the sigmoid, and the rectum. In images 1500, the first (top) row through the seventh (bottom) row respectively show segmentation of the bladder, the prostate, the rectum, the left femur, the right femur, the seminal vesicles, and the uterus. In images 1600, the first (top) row through the seventh (bottom) row respectively show segmentation of the chiasm, the left optic nerve, the right optic nerve, the left lens, the right lens, and left eyeball, and the right eyeball.

Ablation Studies: Ablation studies were conducted on the task2 (bowel datasets) to investigate several important questions regarding COSST.

Figure 17:
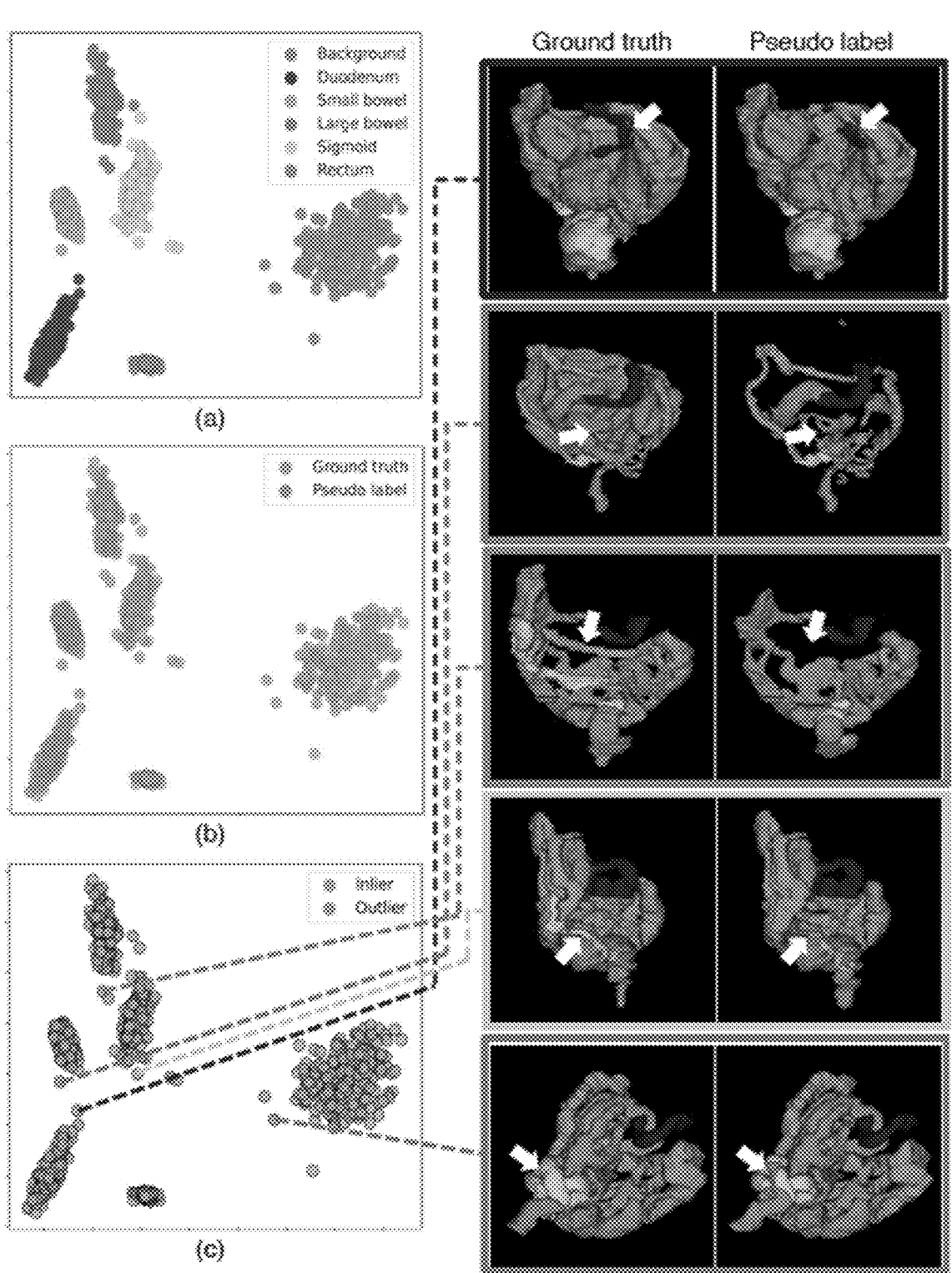
FIG. 17 shows an overview of organwise feature representations.
Figure 18:
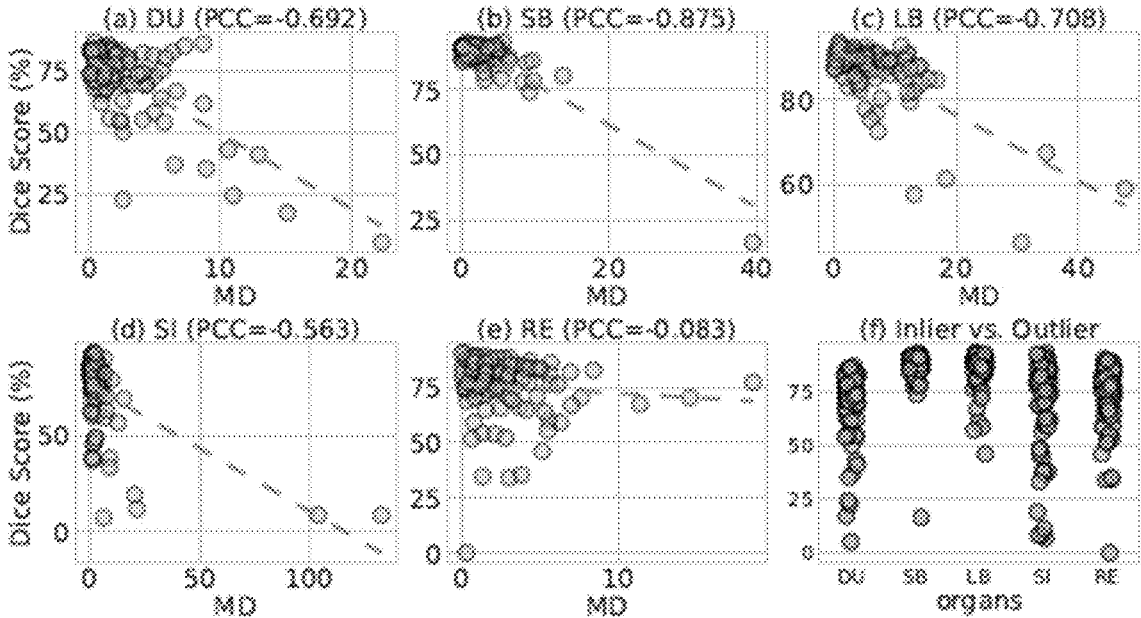
FIG. 18 shows graphs comparing Dice scores of pseudo labels and the Mahalanobis distance.

Effectiveness of Pseudo Label Assessment: In this section, the effectiveness of the pseudo label assessment strategy was assessed. As shown in overview 1700 of FIG. 17, the organ-wise feature representations obtained by Equation (3) are visualized using 2D PCA in panels (a), (b), and (c). In panel (a), it is observed that most feature vectors belonging to the same organ are well clustered. In panel (b), for each organ, the ground truth distribution is highly entangled with the pseudo label distribution. In panel (c), the detected outliers (unreliable pseudo labels) identified by the pseudo label assessment strategy are visualized. Given the additional annotations of the initially unlabeled organs, the quality of the pseudo labels that are identified as outliers are comprehensively evaluated. On the right panel of overview 1700 of FIG. 17, the qualitative comparison shows that the detected pseudo labels have significant differences in shape compared to the ground truth. For quantitative comparison, the Dice scores were computed of all pseudo labels against ground truth and the Pearson Correlation Coefficient (PCC) was calculated between the proposed assessment metric, i.e., Mahalanobis distance, and the Dice scores. FIG. 18 shows graphs 1800 comparing Dice scores of pseudo labels and their corresponding assessment metric (i.e., Mahalanobis distance (MD)). As shown in graphs 1800 of FIG. 18, strong correlations for most organs, i.e., duodenum, small bowel and large bowel, moderate correlation for sigmoid, but weak correlation for rectum was observed. The underlying reason for the weak correlation of rectum may be that the shape of rectum is relatively small and thus more sensitive to shape variations. As shown in panel (a) of FIG. 17, compared to other organs, rectum has a less compact cluster in latent space, which makes it more difficult to yield a high correlation between the quality of pseudo labels and the distance in latent space. Lastly, in graph (f) of FIG. 18, it is clearly seen that most detected outliers are among the pseudo labels with the lowest Dice scores across the entire distribution, further verifying the effectiveness of our strategy.

Effectiveness of Pseudo Label Filtering: In this section, the effectiveness of the different pseudo label filtering schemes for self-training was investigated. Specifically, four schemes were compared, including (1) no filtering: pseudo labels are used without quality control, (2) image-level filtering (ours), (3) voxel-level filtering which has been shown to effectively denoise the pseudo label masks on voxel-level, and (4) the combination of image-level and voxel-level filtering. We report the average Dice scores and ASD of all organs for comparison, as shown in table 1900 of FIG. 19. The following observations were made. First, even with no filtering, self-training with the plain pseudo labels has already improved the performance of the initial unified model (row 1 vs. row 2), demonstrating that both the pseudo label supervision can be used for free performance boost and is complementary to the ground truth-based supervision. Second, self-training performance can be further improved by image-level pseudo label filtering, especially the ASD (row 2 vs. row 3), suggesting that the unreliable pseudo labels may have limited the model performance. Lastly, the experiments show that the voxel-level filtering scheme does not enhance the self-training performance for the specific task (row 4 and 5). This indicates that the noisy pseudo labels may not be reliably fixed via voxel-level denoising and they should rather be entirely excluded from training.

Impact of Training Data Size: In this section, the impact of training data size on different partial-label segmentation methods is explored. Specifically, the competing methods were additionally trained using only 50% and 25% of training data, simulating the scenarios where the size of partially labeled datasets is more limited. As shown in graph 2000 of FIG. 20, the top three benchmark methods, i.e., ME, PLT, and Co-training, were observed to achieve comparable performance with 100% and 50% of training data, while ME outperforms the other two by a large margin at 25%. This suggests that the pseudo label-based approaches, such as PLT and Co-training, may yield suboptimal performance in low-data scenarios if the noisy pseudo labels are not removed. It can also be observed that at 25% training data, COSST achieves slightly better performance than ME. The underlying reason is that the model trained with only 25% training data cannot achieve very satisfactory performance and thus the pseudo labels at low data regime are less reliable, limiting the benefit from pseudo label training. Due to the pseudo label filtering mechanism, the COSST approach does not suffer from performance degradation as PLT and Co-training and can be slightly better than ME at 25%. In summary, compared to the top-performing benchmark methods, COSST is more robust to different training data sizes and stands out as a better option given a new partial-label segmentation task.

Figure 20:
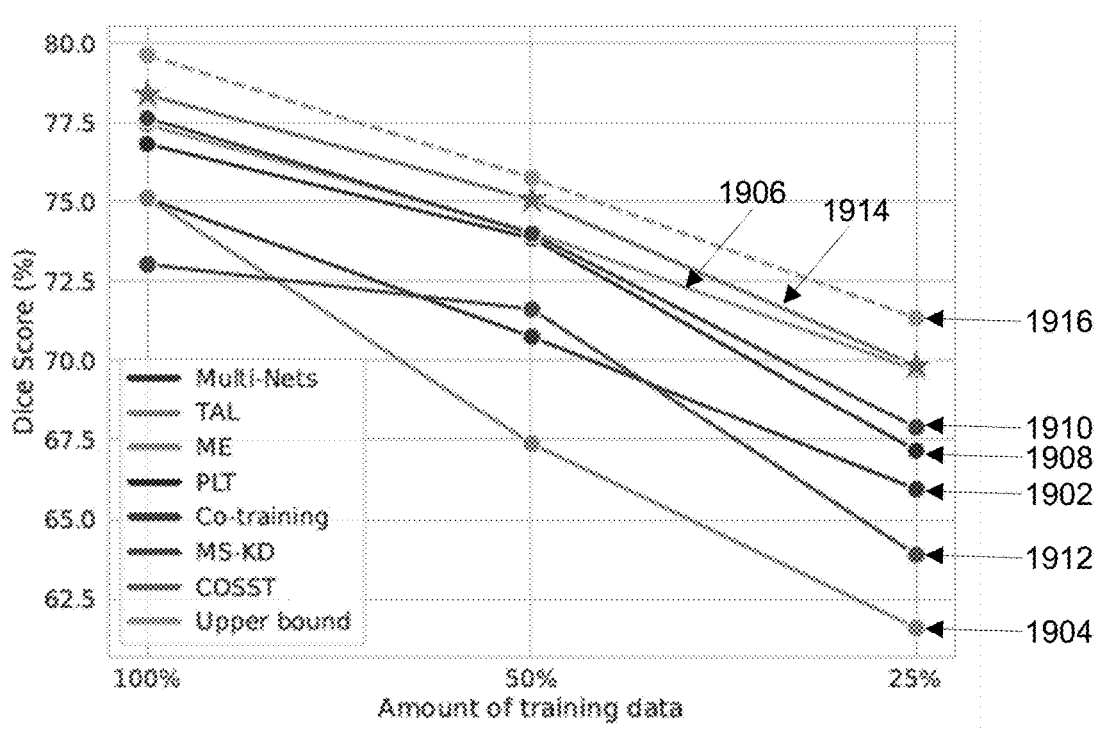
FIG. 20 shows a plot comparing Dice scores with the amount of training data.
Figure 21:
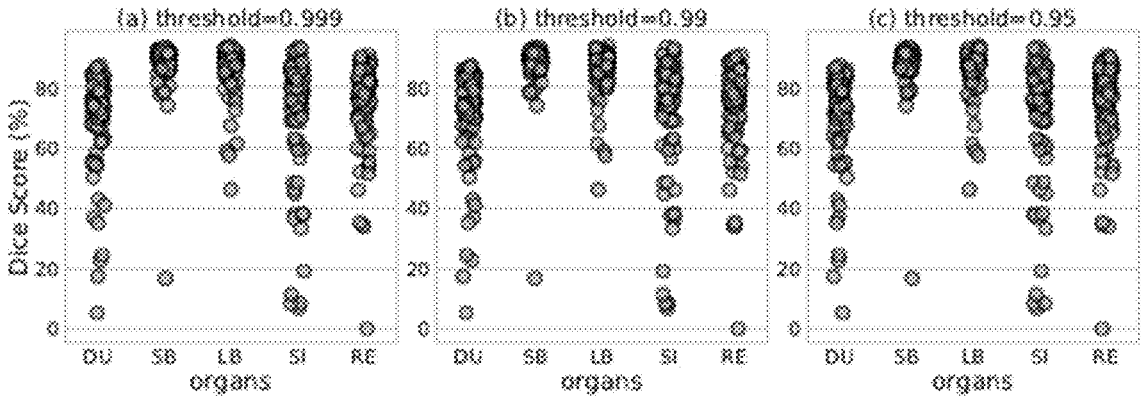
FIG. 21 shows graphs showing outliers detected according to different threshold values.

Impact of the Threshold for Outlier Detection: We conduct experiments to explore the impact of different threshold values for outlier detection using Mahalanobis distance, including 0.999, 0.99 and 0.95. FIG. 20 shows a graph 2000 comparing performance of partial-label segmentation methods with different training data sizes. In graph 2000, plot 2002 represents multi-nets, plot 2004 represents TAL, plot 2006 represents ME, plot 2008 represents PLT, plot 2010 represents Co-training, plot 2012 represents MS-KD, plot 2014 represents COSST, and plot 2016 represents the upper bound. First, as shown in graph 2000 of FIG. 20, the inlier vs. outlier plots are visualized over three threshold values for Mahalanobis distance. It is observed that more data points are considered as outliers as the threshold value decreases. However, we notice that a low threshold such as 0.95, though removing many poor pseudo labels, may also remove some pseudo labels with reasonable dice scores. This finding aligns with the results in graphs 2100 of FIG. 21, which shows outliers detected by different thresholds for the Mahalanobis distance. In graph 2100, the correlation between the Mahalanobis distance and the actual Dice scores is not perfect. To further investigate the impact of thresholds on the segmentation performance, the second stage of COSST was trained with different sets of pseudo labels filtered by different thresholds. The results show that the Dice score on the validation set is improved from 75.45% (first-stage) to 76.32%, 76.18% and 75.81% for threshold values of 0.999, 0.99, and 0.95, respectively. This result suggests that a conservative threshold is more suitable for our pseudo label filtering method such that the most unreliable pseudo labels can be removed without excluding too many reasonable pseudo labels. Therefore, we empirically set the threshold as 0.999 for all our experiments. Though a fixed threshold may not be optimal for every dataset/task, the results show that a threshold of 0.999, determined based on task2, can be reliably used for other tasks in our experiments.

Figure 22:
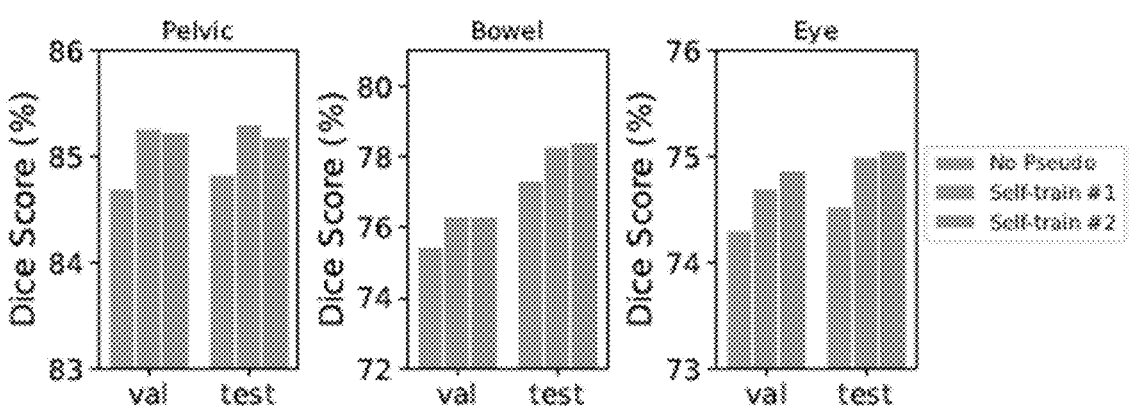
FIG. 22 shows bar graphs comparing performance achieved by different self-training iterations.

Impact of Self-training Iterations: The impact of self-training iterations on model performance on task2-4 was investigated. FIG. 22 shows bar graphs 2200 comparing performance achieved by different self-training iterations on three segmentation tasks. As shown in FIG. 22, self-training typically converges within one or two iterations and the most significant improvement is observed at the first iteration (No Pseudo vs. Self-train #1). Moreover, in the experiments, we find it effective to use the validation performance to determine when to terminate self-training. However, this finding needs to be interpreted carefully because the data distribution of our validation set may be similar to testing set. Other termination criteria may be used to obtain better self-training results.

In the experiments, the partial-label segmentation problem was systematically investigated with both theoretical analyses and empirical evaluations on the prior techniques. Three types of supervision signals were identified for partial-label segmentation and it was shown that integration of three supervision signals using self-training and pseudo label filtering can lead to improved performance.

Unified model vs. Individual models: The experimental results show that the unified models that are trained on all partially labeled datasets achieve better segmentation performance than the Multi-Nets that are separately trained on each individual partial-label dataset. The unified models outperform Multi-Nets especially in the distance-based evaluation metrics, indicating that training on more data (even partially labeled) can help improve the reliability of the segmentation results. The consistent outperformance the partial-label learning is observed on all four segmentation tasks in our experiments and our finding also aligns with the results provided by other studies. Moreover, the results also show that the superiority of unified models is invariant to the amount of training data used (FIG. 20). Besides the improved performance, unified models are more efficient than Multi-Nets as they can segment all organs of interest simultaneously. By contrast, Multi-Nets needs to combine the results from individual models and thus takes longer inference time. Moreover, Multi-Nets may require extra post-processing steps to address conflicting predictions.

Analyses of the Prior Techniques: In this section, the benchmark partial-label segmentation methods were empirically analyzed based on the experimental results. First, the two methods that utilize only the ground truth-based supervision signals, namely TAL and ME, were compared. Compared to TAL which only considers Sup. I, ME imposes an additional supervision (Sup. II) to regularize the predictions of unlabeled organs based on the mutual exclusiveness among organs. In task1, it is observed that TAL and ME achieve highly comparable segmentation results in Dice scores but TAL achieves slightly better results in distance-based metrics. However, in task2-4, we find that ME achieves consistent better segmentation results than TAL and can even surpass the pseudo label-based approaches, e.g., ME outperforms both PLT and Co-training in task3. The underlying reason may be that when multiple organs are annotated in each partially labeled dataset, the mutual exclusiveness can be better used to regularize where the organ cannot overlap and thus reduce the ambiguity among different organs. Second, we compare the approaches that exploit pseudo labels, including PLT, Co-training, and MS- KD. Compared to PLT where pseudo labels are not updated throughout the training process, Co-training uses a pair of co-trained networks to generate pseudo labels for each other and thus pseudo labels can be updated during training. The results show that PLT and Co-training achieve comparable segmentation performance in task1. In task2-4, Co-training is among the top-performing methods and outperforms PLT consistently, suggesting that the quality of pseudo labels plays a key role for pseudo label learning. Besides, we observe unsatisfactory performance for the MS-KD, where the student model is trained solely on the soft pseudo labels generated by the teacher models. The underlying reason may be that the teacher models in MS-KD, i.e., the individual networks trained on each partially labeled dataset (Multi-Nets), are not strong. Hence, it may be necessary to incorporate both soft and hard labels (ground truth) for more effective knowledge distillation.

Third, the results achieved by the conditioned network, DoDNet, were analyzed. Overall, DoDNet achieves comparable segmentation performance to other methods in task1 but suboptimal performance in task2-4. For example, on the bowel datasets, it achieves inferior results on small structures such as duodenum and rectum compared to the methods that use multi-output channel networks. A possible reason could be that in the experiments the same backbone for DoDNet and other competing methods were used, but DoDNet may require a more complex backbone to achieve comparable results. Besides, we notice that DoDNet fails to distinguish the symmetric organs such as left and right femur/optic nerve, i.e., both sides of organs would be segmented when only asked for one side. The underlying reason may be that the conditioned networks by design learn each organ independently and thus may ignore the correlation among organs. By contrast, multi-output channel networks, which segment all organs simultaneously, naturally capture the relationships among different organs. However, this suggests that DoDNet can be better at the segmentation tasks where organs are less correlated. For example, in task3 (table 1200 of FIG. 12), it is observed that DoDNet shows superior segmentation results on seminal vesicles and uterus, which are less correlated to other organs because they do not always appear due to gender difference. Lastly, since each organ is trained separately, DoDNet may be less efficient to train on the partially labeled dataset labeled with multiple organs. To summarize, the conditioned network DoDNet may need a more complex backbone to achieve optimal performance and is better at independent segmentation tasks.

Analyses of COSST: The development of the proposed COSST is motivated by taking advantage of the effective components based on the empirical analyses above. Specifically, COSST is built upon a multi-output channel network by incorporating (1) mutual exclusiveness for regularization, (2) pseudo label for training, and (3) better pseudo labels for improved performance, where (1) and (2) correspond to the integration of comprehensive supervision signals and (3) corresponds to self-training and pseudo label filtering. In table 1000 to 1300 of FIGS. 10 to 13, it is shows that the proposed COSST outperforms the top-performing benchmark methods, i.e., ME and Cotraining, on all four segmentation tasks with different degrees of improvement. Besides, in graphs 1800 of FIG. 18, it is observed that ME outperforms Co-training by a large margin when the amount of training data is small, but slightly underperforms Co-training when more training data is available. Hence, given a new partial-label segmentation task, it is not clear which method in the literature should be adopted due to their sensitivity to the training data size. By contrast, COSST stands out as a more reliable option as it achieves consistent better performance than ME and Co-training regardless of the amount of training data.

The effectiveness of pseudo label assessment approach with in-depth analyses was demonstrated. Specifically, it was shown that given the distribution of the ground truth labels, the quality of the unlabeled pseudo labels can be successfully assessed by using outlier detection in latent space. The COSST approach can thus be extend to other fields where pseudo labeling is important, such as semi-supervised learning and domain adaptation.

Learning from partially labeled datasets is important to emerging medical foundation models, which aim to train a universal segmentation model from large-scale datasets collected from different institutions. The types of supervision signals and the training strategy presented in herein study can thus be used in foundation model development. Further, modern foundation models in the computer vision community may utilize self-training with pseudo labels for increased performance. In addition, pseudo label training may be applied for the cross-modality setting.

Embodiments described herein are described with respect to the claimed systems as well as with respect to the claimed methods. Features, advantages or alternative embodiments herein can be assigned to the other claimed objects and vice versa. In other words, claims and embodiments for the systems can be improved with features described or claimed in the context of the respective methods. In this case, the functional features of the method are implemented by physical units of the system.

Furthermore, certain embodiments described herein are described with respect to methods and systems utilizing trained machine learning models, as well as with respect to methods and systems for providing trained machine learning models. Features, advantages or alternative embodiments herein can be assigned to the other claimed objects and vice versa. In other words, claims and embodiments for providing trained machine learning models can be improved with features described or claimed in the context of utilizing trained machine learning models, and vice versa. In particular, datasets used in the methods and systems for utilizing trained machine learning models can have the same properties and features as the corresponding datasets used in the methods and systems for providing trained machine learning models, and the trained machine learning models provided by the respective methods and systems can be used in the methods and systems for utilizing the trained machine learning models.

In general, a trained machine learning model mimics cognitive functions that humans associate with other human minds. In particular, by training based on training data the machine learning model is able to adapt to new circumstances and to detect and extrapolate patterns. Another term for "trained machine learning model" is "trained function."

In general, parameters of a machine learning model can be adapted by means of training. In particular, supervised training, semi-supervised training, unsupervised training, reinforcement learning and/or active learning can be used. Furthermore, representation learning (an alternative term is "feature learning") can be used. In particular, the parameters of the machine learning models can be adapted iteratively by several steps of training. In particular, within the training a certain cost function can be minimized. In particular, within the training of a neural network the backpropagation algorithm can be used.

In particular, a machine learning model, such as, e.g., the segmentation model 104 of FIG. 1, the machine learning based networks 210, 212, and 218 of FIG. 2, the machine learning based models utilized at steps 304, 306, 308, and 310 of FIG. 3, the machine learning based feature extractor network 408 of FIG. 4, the unified model of FIG. 5, the teacher models 602 and student model 604 of FIG. 6, and the machine learning based model utilized at step 704 of FIG. 7, can comprise, for example, a neural network, a support vector machine, a decision tree and/or a Bayesian network, and/or the machine learning model can be based on, for example, k-means clustering, Q-learning, genetic algorithms and/or association rules. In particular, a neural network can be, e.g., a deep neural network, a convolutional neural network or a convolutional deep neural network. Furthermore, a neural network can be, e.g., an adversarial network, a deep adversarial network and/or a generative adversarial network.

Figure 23:
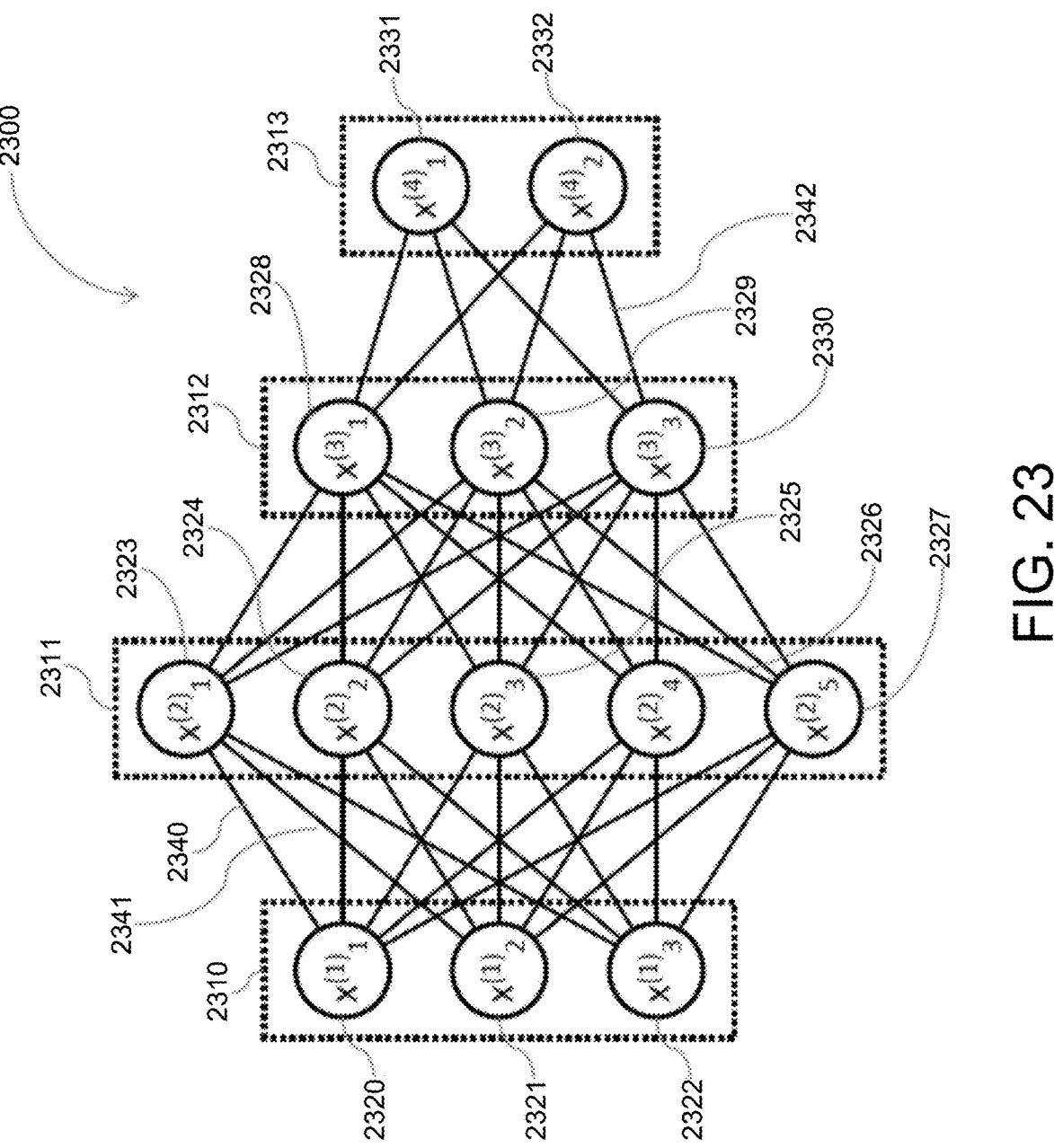
FIG. 23 shows an exemplary artificial neural network that may be used to implement one or more embodiments.

FIG. 23 shows an embodiment of an artificial neural network 2300 that may be used to implement one or more machine learning models described herein. Alternative terms for "artificial neural network" are "neural network", "artificial neural net" or "neural net".

The artificial neural network 2300 comprises nodes 2320, . . . , 2332 and edges 2340, . . . 2342, wherein each edge 2340, . . . , 2342 is a directed connection from a first node 2320, . . . , 2332 to a second node 2320, . . . , 2332. In general, the first node 2320, . . . , 2332 and the second node 2320, . . . , 2332 are different nodes 2320, 2332, it is also possible that the first node 2320, . . . , 2332 and the second node 2320, . . . , 2332 are identical. For example, in FIG. 23 the edge 2340 is a directed connection from the node 2320 to the node 2323, and the edge 2342 is a directed connection from the node 2330 to the node 2332. An edge 2340, . . . , 2342 from a first node 2320, . . . , 2332 to a second node 2320, . . . , 2332 is also denoted as "ingoing edge" for the second node 2320, . . . , 2332 and as "outgoing edge" for the first node 2320, . . . , 2332.

In this embodiment, the nodes 2320, . . . , 2332 of the artificial neural network 2300 can be arranged in layers 2310, . . . , 2313, wherein the layers can comprise an intrinsic order introduced by the edges 2340, . . . , 2342 between the nodes 2320, . . . , 2332. In particular, edges 2340, . . . , 2342 can exist only between neighboring layers of nodes. In the displayed embodiment, there is an input layer 2310 comprising only nodes 2320, . . . , 2322 without an incoming edge, an output layer 2313 comprising only nodes 2331, 2332 without outgoing edges, and hidden layers 2311, 2312 in-between the input layer 2310 and the output layer 2313. In general, the number of hidden layers 2311, 2312 can be chosen arbitrarily. The number of nodes 2320, . . . , 2322 within the input layer 2310 usually relates to the number of input values of the neural network, and the number of nodes 2331, 2332 within the output layer 2313 usually relates to the number of output values of the neural network.

In particular, a (real) number can be assigned as a value to every node 2320, . . . , 2332 of the neural network 2300. Here, $x^{(n)}i$ denotes the value of the i-th node 2320, . . . 2332 of the n-th layer 2310, . . . , 2313. The values of the nodes 2320, . . . , 2322 of the input layer 2310 are equivalent to the input values of the neural network 2300, the values of the nodes 2331, 2332 of the output layer 2313 are equivalent to the output value of the neural network 2300. Furthermore, each edge 2340, . . . , 2342 can comprise a weight being a real number, in particular, the weight is a real number within the interval [−1, 1] or within the interval [0, 1]. Here, $w^{(m,n)}_{i,j}$ denotes the weight of the edge between the i-th node

2320, . . . , 2332 of the m-th layer 2310, . . . , 2313 and the j-th node 2320, . . . , 2332 of the n-th layer 2310, . . . , 2313. Furthermore, the abbreviation $w^{(n)}_{i,j}$ is defined for the weight $w^{(n,n+1)}_{i,j}$.

In particular, to calculate the output values of the neural network 2300, the input values are propagated through the neural network. In particular, the values of the nodes 2320, . . . , 2332 of the (n+1)-th layer 2310, . . . , 2313 can be calculated based on the values of the nodes 2320, 2332 of the n-th layer 2310, . . . , 2313 by $$x^{(n+1)}_j = f\left( \sum_i x^{(n)}_i \cdot w^{(n)}_{i,j} \right).$$

Herein, the function f is a transfer function (another term is "activation function"). Known transfer functions are step functions, sigmoid function (e.g., the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 2310 are given by the input of the neural network 2300, wherein values of the first hid-den layer 2311 can be calculated based on the values of the input layer 2310 of the neural network, wherein values of the second hidden layer 2312 can be calculated based in the values of the first hidden layer 2311, etc.

In order to set the values $w^{(m,n)}_{i,j}$ for the edges, the neural network 2300 has to be trained using training data. In particular, training data comprises training input data and training output data (denoted as $t_i$). For a training step, the neural network 2300 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 2300 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta^{(n)}_j = \left( \sum_k \delta^{(n+1)}_k \cdot w^{(n+1)}_{j,k} \right) \cdot f'\left( \sum_i x^{(n)}_i \cdot w^{(n)}_{i,j} \right)$$

based on $\delta^{(n+1)}_j$, if the (n+1)-th layer is not the output layer, and $$\delta^{(n)}_j = \left( x^{(n+1)}_j - t^{(n+1)}_j \right) \cdot f'\left( x^{(n)}_i \cdot w^{(n)}_{i,j} \right)$$

if the (n+1)-th layer is the output layer 2313, wherein f' is the first derivative of the activation function, and $t^{(n+1)}_j$ is the comparison training value for the j-th node of the output layer 2313.

A convolutional neural network is a neural network that uses a convolution operation instead general matrix multiplication in at least one of its layers (so-called "convolutional layer"). In particular, a convolutional layer performs a dot product of one or more convolution kernels with the convolutional layer's input data/image, wherein the entries of the one or more convolution kernel are the parameters or weights that are adapted by training. In particular, one can use the Frobenius inner product and the ReLU activation function. A convolutional neural network can comprise additional layers, e.g., pooling layers, fully connected layers, and normalization layers.

By using convolutional neural networks input images can be processed in a very efficient way, because a convolution operation based on different kernels can extract various image features, so that by adapting the weights of the convolution kernel the relevant image features can be found during training. Furthermore, based on the weight-sharing in the convolutional kernels less parameters need to be trained, which prevents overfitting in the training phase and allows to have faster training or more layers in the network, improving the performance of the network.

Figure 24:
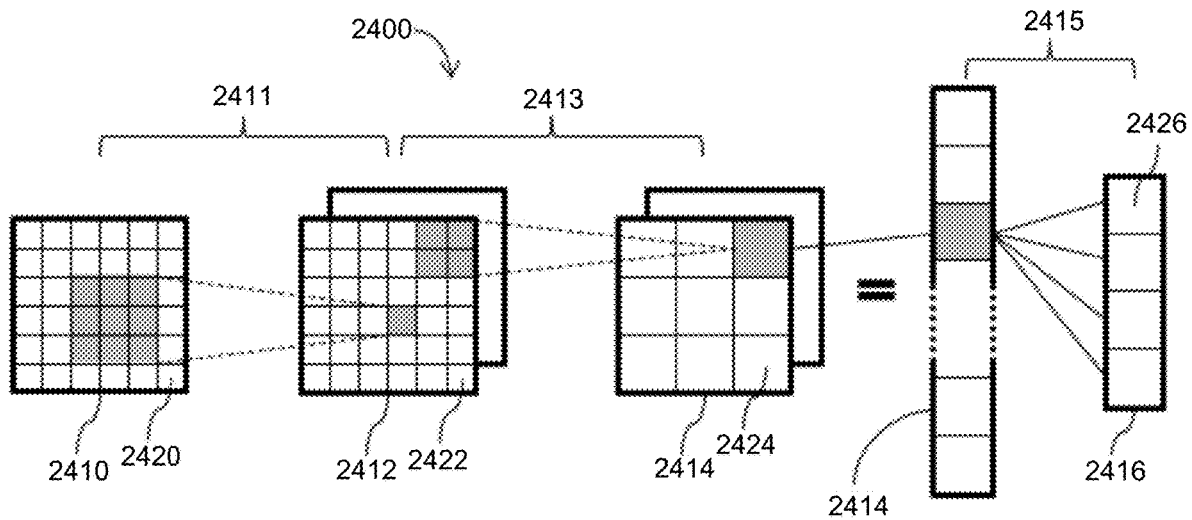
FIG. 24 shows a convolutional neural network that may be used to implement one or more embodiments.

FIG. 24 shows an embodiment of a convolutional neural network 2400 that may be used to implement one or more machine learning models described herein. In the displayed embodiment, the convolutional neural network comprises 2400 an input node layer 2410, a convolutional layer 2411, a pooling layer 2413, a fully connected layer 2414 and an output node layer 2416, as well as hidden node layers 2412, 2414. Alternatively, the convolutional neural network 2400 can comprise several convolutional layers 2411, several pooling layers 2413 and several fully connected layers 2415, as well as other types of layers. The order of the layers can be chosen arbitrarily, usually fully connected layers 2415 are used as the last layers before the output layer 2416.

In particular, within a convolutional neural network 2400 nodes 2420, 2422, 2424 of a node layer 2410, 2412, 2414 can be considered to be arranged as a d-dimensional matrix or as a d-dimensional image. In particular, in the two-dimensional case the value of the node 2420, 2422, 2424 indexed with i and j in the n-th node layer 2410, 2412, 2414 can be denoted as x(n)[i, j]. However, the arrangement of the nodes 2420, 2422, 2424 of one node layer 2410, 2412, 2414 does not have an effect on the calculations executed within the convolutional neural network 2400 as such, since these are given solely by the structure and the weights of the edges.

A convolutional layer 2411 is a connection layer between an anterior node layer 2410 (with node values $x(n-1)$) and a posterior node layer 2412 (with node values $x(n)$). In particular, a convolutional layer 2411 is characterized by the structure and the weights of the incoming edges forming a convolution operation based on a certain number of kernels. In particular, the structure and the weights of the edges of the convolutional layer 2411 are chosen such that the values $x(n)$ of the nodes 2422 of the posterior node layer 2412 are calculated as a convolution $x(n)=K*x(n-1)$ based on the values $x(n-1)$ of the nodes 2420 anterior node layer 2410, where the convolution $*$ is defined in the two-dimensional case as $$x_k^{(n)}[i, j] = \left(K * x^{(n-1)}\right)[i, j] = \sum_{i'} \sum_{j'} K[i', j'] \cdot x^{(n-1)}[i - i', j - j'].$$

Here the kernel K is a d-dimensional matrix (in this embodiment, a two-dimensional matrix), which is usually small compared to the number of nodes 2420, 2422 (e.g., a 3×3 matrix, or a 5×5 matrix). In particular, this implies that the weights of the edges in the convolution layer 2411 are not independent, but chosen such that they produce said convolution equation. In particular, for a kernel being a 3×3 matrix, there are only 9 independent weights (each entry of the kernel matrix corresponding to one independent weight), irrespectively of the number of nodes 2420, 2422 in the anterior node layer 2410 and the posterior node layer 2412.

In general, convolutional neural networks 2400 use node layers 2410, 2412, 2414 with a plurality of channels, in particular, due to the use of a plurality of kernels in convolutional layers 2411. In those cases, the node layers can be considered as (d+1)-dimensional matrices (the first dimension indexing the channels). The action of a convolutional layer 2411 is then a two-dimensional example defined as $$x^{(n)_b}[i, j] =$$
$$\sum_a K_{a,b} * x^{(n-1)_a}[i, j] = \sum_a \sum_{i'} \sum_{j'} K_{a,b}[i', j'] \cdot x^{(n-1)_a}[i - i', j - j']$$

where $x^{(n-1)_a}$ corresponds to the a-th channel of the anterior node layer 2410, $x^{(n)_b}$ corresponds to the b-th channel of the posterior node layer 2412 and $K_{a,b}$ corresponds to one of the kernels. If a convolutional layer 2411 acts on an anterior node layer 2410 with A channels and outputs a posterior node layer 2412 with B channels, there are A·B independent d-dimensional kernels $K_{a,b}$.

In general, in convolutional neural networks 2400 activation functions are used. In this embodiment re ReLU (acronym for "Rectified Linear Units") is used, with $R(z)= max(0, z)$, so that the action of the convolutional layer 2411 in the two-dimensional example is $$x^{(n)_b}[i, j] = R\left(\sum_a \left(K_{a,b} * x^{(n-1)_a}\right)[i, j]\right) =$$
$$R\left(\sum_a \sum_{i'} \sum_{j'} K_{a,b}[i', j'] \cdot x^{(n-1)_a}[i - i', j - j']\right)$$

It is also possible to use other activation functions, e.g., ELU (acronym for "Exponential Linear Unit"), LeakyReLU, Sigmoid, Tanh or Softmax.

In the displayed embodiment, the input layer 2410 comprises 36 nodes 2420, arranged as a two-dimensional 6×6 matrix. The first hidden node layer 2412 comprises 72 nodes 2422, arranged as two two-dimensional 6×6 matrices, each of the two matrices being the result of a convolution of the values of the input layer with a 3×3 kernel within the convolutional layer 2411. Equivalently, the nodes 2422 of the first hidden node layer 2412 can be interpreted as arranged as a three-dimensional 2×6×6 matrix, wherein the first dimension correspond to the channel dimension.

The advantage of using convolutional layers 2411 is that spatially local correlation of the input data can exploited by enforcing a local connectivity pattern between nodes of adjacent layers, in particular by each node being connected to only a small region of the nodes of the preceding layer.

A pooling layer 2413 is a connection layer between an anterior node layer 2412 (with node values $x(n-1)$) and a posterior node layer 2414 (with node values $x(n)$). In particular, a pooling layer 2413 can be characterized by the structure and the weights of the edges and the activation function forming a pooling operation based on a non-linear pooling function f. For example, in the two-dimensional case the values x(n) of the nodes 2424 of the posterior node layer 2414 can be calculated based on the values x(n-1) of the nodes 2422 of the anterior node layer 2412 as $$x^{(n)}{}_b\,[i,\,j] = f\!\left(x^{(n-1)}[id_1,\,jd_2],\,\ldots\,,\,x^{(n-1)}{}_b\,[(i+1)d_1{-}1,\,(j+1)d_2{-}1]\right)$$

In other words, by using a pooling layer 2413 the number of nodes 2422, 2424 can be reduced, by re-placing a number d1·d2 of neighboring nodes 2422 in the anterior node layer 2412 with a single node 2422 in the posterior node layer 2414 being calculated as a function of the values of said number of neighboring nodes. In particular, the pooling function f can be the max-function, the average or the L2-Norm. In particular, for a pooling layer 2413 the weights of the incoming edges are fixed and are not modified by training.

The advantage of using a pooling layer 2413 is that the number of nodes 2422, 2424 and the number of parameters is reduced. This leads to the amount of computation in the network being reduced and to a control of overfitting.

In the displayed embodiment, the pooling layer 2413 is a max-pooling layer, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

In general, the last layers of a convolutional neural network 2400 are fully connected layers 2415. A fully connected layer 2415 is a connection layer between an anterior node layer 2414 and a posterior node layer 2416. A fully connected layer 2413 can be characterized by the fact that a majority, in particular, all edges between nodes 2414 of the anterior node layer 2414 and the nodes 2416 of the posterior node layer are present, and wherein the weight of each of these edges can be adjusted individually.

In this embodiment, the nodes 2424 of the anterior node layer 2414 of the fully connected layer 2415 are displayed both as two-dimensional matrices, and additionally as non-related nodes (indicated as a line of nodes, wherein the number of nodes was reduced for a better presentability). This operation is also denoted as "flattening". In this embodiment, the number of nodes 2426 in the posterior node layer 2416 of the fully connected layer 2415 smaller than the number of nodes 2424 in the anterior node layer 2414. Alternatively, the number of nodes 2426 can be equal or larger.

Furthermore, in this embodiment the Softmax activation function is used within the fully connected layer 2415. By applying the Softmax function, the sum the values of all nodes 2426 of the output layer 2416 is 1, and all values of all nodes 2426 of the output layer 2416 are real numbers between 0 and 1. In particular, if using the convolutional neural network 2400 for categorizing input data, the values of the output layer 2416 can be interpreted as the probability of the input data falling into one of the different categories.

In particular, convolutional neural networks 2400 can be trained based on the backpropagation algorithm. For preventing overfitting, methods of regularization can be used, e.g., dropout of nodes 2420, . . . , 2424, stochastic pooling, use of artificial data, weight decay based on the L1 or the L2 norm, or max norm constraints.

According to an aspect, the machine learning model may comprise one or more residual networks (ResNet). In particular, a ResNet is an artificial neural network comprising at least one jump or skip connection used to jump over at least one layer of the artificial neural network. In particular, a ResNet may be a convolutional neural network comprising one or more skip connections respectively skipping one or more convolutional layers. According to some examples, the ResNets may be represented as m-layer ResNets, where m is the number of layers in the corresponding architecture and, according to some examples, may take values of 34, 50, 101, or 152. According to some examples, such an m-layer ResNet may respectively comprise (m−2)/2 skip connections.

A skip connection may be seen as a bypass which directly feeds the output of one preceding layer over one or more bypassed layers to a layer succeeding the one or more bypassed layers. Instead of having to directly fit a desired mapping, the bypassed layers would then have to fit a residual mapping "balancing" the directly fed output.

Fitting the residual mapping is computationally easier to optimize than the directed mapping. What is more, this alleviates the problem of vanishing/exploding gradients during optimization upon training the machine learning models: if a bypassed layer runs into such problems, its contribution may be skipped by regularization of the directly fed output. Using ResNets thus brings about the advantage that much deeper networks may be trained.

In particular, a recurrent machine learning model is a machine learning model whose output does not only depend on the input value and the parameters of the machine learning model adapted by the training process, but also on a hidden state vector, wherein the hidden state vector is based on previous inputs used on for the recurrent machine learning model. In particular, the recurrent machine learning model can comprise additional storage states or additional structures that incorporate time delays or comprise feedback loops.

In particular, the underlying structure of a recurrent machine learning model can be a neural network, which can be denoted as recurrent neural network. Such a recurrent neural network can be described as an artificial neural network where connections between nodes form a directed graph along a temporal sequence. In particular, a recurrent neural network can be interpreted as directed acyclic graph. In particular, the recurrent neural network can be a finite impulse recurrent neural network or an infinite impulse recurrent neural network (wherein a finite impulse network can be unrolled and replaced with a strictly feedforward neural network, and an infinite impulse network cannot be unrolled and replaced with a strictly feedforward neural network).

In particular, training a recurrent neural network can be based on the BPTT algorithm (acronym for "backpropagation through time"), on the RTRL algorithm (acronym for "real-time recurrent learning") and/or on genetic algorithms.

By using a recurrent machine learning model input data comprising sequences of variable length can be used. In particular, this implies that the method cannot be used only for a fixed number of input datasets (and needs to be trained differently for every other number of input datasets used as input), but can be used for an arbitrary number of input datasets. This implies that the whole set of training data, independent of the number of input datasets contained in different sequences, can be used within the training, and that training data is not reduced to training data corresponding to a certain number of successive input datasets.

Figure 25:
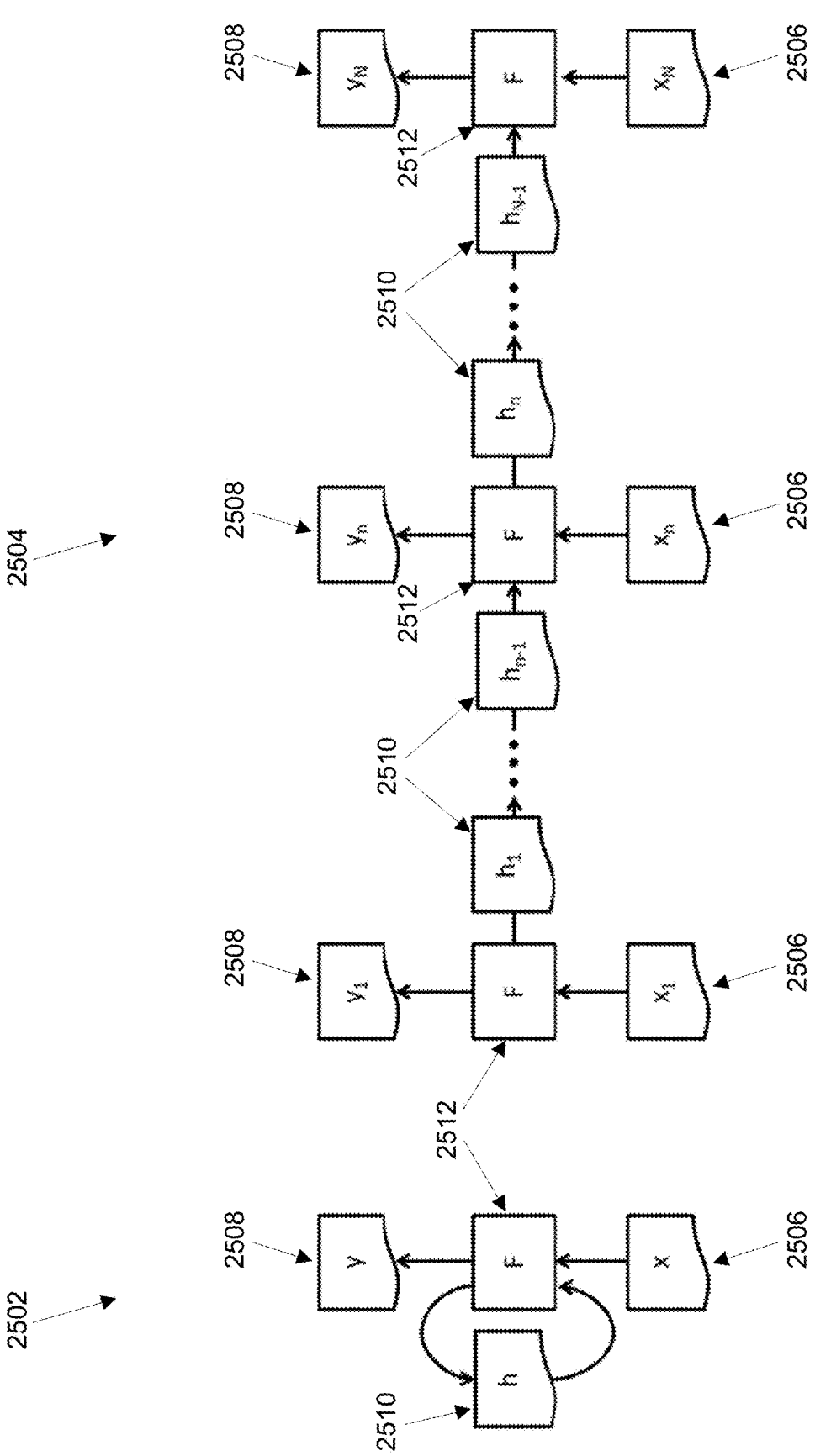
FIG. 25 shows a schematic structure of a recurrent machine learning model that may be used to implement one or more embodiments.

FIG. 25 shows the schematic structure of a recurrent machine learning model F, both in a recurrent representation 2502 and in an unfolded representation 2504, that may be used to implement one or more machine learning models described herein. The recurrent machine learning model takes as input several input datasets x, $x_1, \ldots, x_N$ 2506 and creates a corresponding set of output datasets y, $y_1, \ldots, y_N$ 2508. Furthermore, the output depends on a so-called hidden vector h, $h_1, \ldots, h_N$ 2510, which implicitly comprises information about input datasets previously used as input for the recurrent machine learning model F 2512. By using these hidden vectors h, $h_1, \ldots, h_N$ 2510, a sequentiality of the input datasets can be leveraged.

In a single step of the processing, the recurrent machine learning model F 2512 takes as input the hidden vector $h_{n-1}$ created within the previous step and an input dataset $x_n$. Within this step, the recurrent machine learning model F generates as output an updated hidden vector $h_n$ and an output dataset $y_n$. In other words, one step of processing calculates $(y_n, h_n) = F(x_n, h_{n-1})$, or by splitting the recurrent machine learning model F 2512 into a part F(y) calculating the output data and F(h) calculating the hidden vector, one step of processing calculates $y_n = F^{(y)}(x_n, h_{n-1})$ and $h_n = F(h)$ $(x_n, h_{n-1})$. For the first processing step, $h_0$ can be chosen randomly or filled with all entries being zero. The parameters of the recurrent machine learning model F 2512 that were trained based on training datasets before do not change between the different processing steps.

In particular, the output data and the hidden vector of a processing step depend on all the previous input datasets used in the previous steps. $y_n = F^{(y)}(x_n, F^{(h)}(x_{n-1}, h_{n-2}))$ and $h_n = F(h)(x_n, F^{(h)}(x_{n-1}, h_{n-2}))$.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatuses, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatuses, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-7. Certain steps or functions of the methods and workflows described herein, including one or more of the steps or functions of FIGS. 1-7, may be performed by a server or by another processor in a network-based cloud-computing system. Certain steps or functions of the methods and workflows described herein, including one or more of the steps of FIGS. 1-7, may be performed by a client computer in a network-based cloud computing system. The steps or functions of the methods and workflows described herein, including one or more of the steps of FIGS. 1-7, may be performed by a server and/or by a client computer in a network-based cloud computing system, in any combination.

Systems, apparatuses, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-7, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

A high-level block diagram of an example computer 2602 that may be used to implement systems, apparatuses, and methods described herein is depicted in FIG. 26. Computer 2602 includes a processor 2604 operatively coupled to a data storage device 2612 and a memory 2610. Processor 2604 controls the overall operation of computer 2602 by executing computer program instructions that define such operations. The computer program instructions may be stored in data storage device 2612, or other computer readable medium, and loaded into memory 2610 when execution of the computer program instructions is desired. Thus, the method and workflow steps or functions of FIGS. 1-7 can be defined by the computer program instructions stored in memory 2610 and/or data storage device 2612 and controlled by processor 2604 executing the computer program instructions. For example, the computer program instructions can be implemented as computer executable code programmed by one skilled in the art to perform the method and workflow steps or functions of FIGS. 1-7. Accordingly, by executing the computer program instructions, the processor 2604 executes the method and workflow steps or functions of FIGS. 1-7. Computer 2602 may also include one or more network interfaces 2606 for communicating with other devices via a network. Computer 2602 may also include one or more input/output devices 2608 that enable user interaction with computer 2602 (e.g., display, keyboard, mouse, speakers, buttons, etc.).

Processor 2604 may include both general and special purpose microprocessors, and may be the sole processor or one of multiple processors of computer 2602. Processor 2604 may include one or more central processing units (CPUs), for example. Processor 2604, data storage device 2612, and/or memory 2610 may include, be supplemented by, or incorporated in, one or more application-specific integrated circuits (ASICs) and/or one or more field programmable gate arrays (FPGAs).

Data storage device 2612 and memory 2610 each include a tangible non-transitory computer readable storage medium. Data storage device 2612, and memory 2610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 2608 may include peripherals, such as a printer, scanner, display screen, etc. For example, input/output devices 2608 may include a display device such as a cathode ray tube (CRT) or liquid crystal display (LCD) monitor for displaying information to the user, a keyboard, and a pointing device such as a mouse or a trackball by which the user can provide input to computer 2602.

An image acquisition device 2614 can be connected to the computer 2602 to input image data (e.g., medical images) to the computer 2602. It is possible to implement the image acquisition device 2614 and the computer 2602 as one device. It is also possible that the image acquisition device 2614 and the computer 2602 communicate wirelessly through a network. In a possible embodiment, the computer 2602 can be located remotely with respect to the image acquisition device 2614.

Any or all of the systems, apparatuses, and methods discussed herein may be implemented using one or more computers such as computer 2602.

One skilled in the art will recognize that an implementation of an actual computer or computer system may have other structures and may contain other components as well, and that FIG. 26 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The following is a list of non-limiting illustrative embodiments disclosed herein:

Illustrative embodiment 1. A computer-implemented method comprising: receiving one or more input medical images; performing a medical imaging analysis task based on the one or more input medical images using a machine learning based model; and outputting results of the medical imaging analysis task, wherein the machine learning based model is trained by: receiving one or more training medical images and ground truth labels identifying one or more anatomical objects in the one or more training medical images, training the machine learning based model for performing the medical imaging analysis task based on the one or more training medical images and the ground truth labels, generating pseudo labels identifying the one or more anatomical objects in the one or more training medical images using the trained machine learning based model, and fine-tuning the trained machine learning based model for performing the medical imaging analysis task based on the one or more training medical images, the ground truth labels, and the generated pseudo labels.

Illustrative embodiment 2. The computer-implemented method according to illustrative embodiment 1, wherein the machine learning based model is further trained by: filtering the generated pseudo labels based on a comparison between 1) each of the generated pseudo labels identifying a particular anatomical object in the one or more training medical images and 2) a distribution of the ground truth labels identifying the particular anatomical object in the one or more training medical images, wherein fine-tuning the trained machine learning based model for performing the medical imaging analysis task based on the one or more training medical images, the ground truth labels, and the generated pseudo labels comprises fine-tuning the trained machine learning based model for performing the medical imaging analysis task based on the filtered pseudo labels.

Illustrative embodiment 3. The computer-implemented method according to illustrative embodiment 2, wherein filtering the generated pseudo labels based on a comparison between 1) each of the generated pseudo labels identifying a particular anatomical object in the one or more training medical images and 2) a distribution of the ground truth labels identifying the particular anatomical object in the one or more training medical images comprises: determining a feature representation of each of the generated pseudo labels using a feature extractor model of the machine learning based model; determining a distance between a) the feature representation of each of the generated pseudo labels identifying the particular anatomical object in the one or more training medical images and b) the distribution of the ground truth labels identifying the particular anatomical object in the one or more training medical images; and filtering the generated pseudo labels based on a comparison between the distances and a threshold.

Illustrative embodiment 4. The computer-implemented method according to any one of illustrative embodiments 2-3, wherein the machine learning based model is further trained by: repeating the generating, the filtering, and the fine-tuning for a plurality of iterations.

Illustrative embodiment 5. The computer-implemented method according to any one of illustrative embodiments 1-4, wherein fine-tuning the trained machine learning based model for performing the medical imaging analysis task based on the one or more training medical images, the ground truth labels, and the generated pseudo labels comprises: fine-tuning the trained machine learning based model to maximize an overlap between a predicted location of the one or more anatomical objects and a location defined in the ground truth labels.

Illustrative embodiment 6. The computer-implemented method according to any one of illustrative embodiments 1-5, wherein fine-tuning the trained machine learning based model for performing the medical imaging analysis task based on the one or more training medical images, the ground truth labels, and the generated pseudo labels comprises: fine-tuning the trained machine learning based model to maximize an overlap between a predicted location of unlabeled anatomical objects and a location defined in the pseudo labels for the unlabeled anatomical objects.

Illustrative embodiment 7. The computer-implemented method according to any one of illustrative embodiments 1-6, wherein the medical imaging analysis task is segmentation.

Illustrative embodiment 8. An apparatus comprising: means for receiving one or more input medical images; means for performing a medical imaging analysis task based on the one or more input medical images using a machine learning based model; and means for outputting results of the medical imaging analysis task, wherein the machine learning based model is trained by: receiving one or more training medical images and ground truth labels identifying one or more anatomical objects in the one or more training medical images, training the machine learning based model for performing the medical imaging analysis task based on the one or more training medical images and the ground truth labels, generating pseudo labels identifying the one or more anatomical objects in the one or more training medical images using the trained machine learning based model, and fine-tuning the trained machine learning based model for performing the medical imaging analysis task based on the one or more training medical images, the ground truth labels, and the generated pseudo labels.

Illustrative embodiment 9. The apparatus according to illustrative embodiment 8, wherein the machine learning based model is further trained by: filtering the generated pseudo labels based on a comparison between 1) each of the generated pseudo labels identifying a particular anatomical object in the one or more training medical images and 2) a distribution of the ground truth labels identifying the particular anatomical object in the one or more training medical images, wherein fine-tuning the trained machine learning based model for performing the medical imaging analysis task based on the one or more training medical images, the ground truth labels, and the generated pseudo labels comprises fine-tuning the trained machine learning based model for performing the medical imaging analysis task based on the filtered pseudo labels.

Illustrative embodiment 10. The apparatus according to illustrative embodiment 9, wherein filtering the generated pseudo labels based on a comparison between 1) each of the generated pseudo labels identifying a particular anatomical object in the one or more training medical images and 2) a distribution of the ground truth labels identifying the particular anatomical object in the one or more training medical images comprises: determining a feature representation of each of the generated pseudo labels using a feature extractor model of the machine learning based model; determining a distance between a) the feature representation of each of the generated pseudo labels identifying the particular anatomical object in the one or more training medical images and b) the distribution of the ground truth labels identifying the particular anatomical object in the one or more training medical images; and filtering the generated pseudo labels based on a comparison between the distances and a threshold.

Illustrative embodiment 11. The apparatus according to any one of illustrative embodiments 9-10, wherein the machine learning based model is further trained by: repeating the generating, the filtering, and the fine-tuning for a plurality of iterations.

Illustrative embodiment 12. A non-transitory computer-readable storage medium comprising instructions which, when executed by a computer, cause the computer to carry out operations comprising: receiving one or more input medical images; performing a medical imaging analysis task based on the one or more input medical images using a machine learning based model; and outputting results of the medical imaging analysis task, wherein the machine learning based model is trained by: receiving one or more training medical images and ground truth labels identifying one or more anatomical objects in the one or more training medical images, training the machine learning based model for performing the medical imaging analysis task based on the one or more training medical images and the ground truth labels, generating pseudo labels identifying the one or more anatomical objects in the one or more training medical images using the trained machine learning based model, and fine-tuning the trained machine learning based model for performing the medical imaging analysis task based on the one or more training medical images, the ground truth labels, and the generated pseudo labels.

Illustrative embodiment 13. The non-transitory computer-readable storage medium illustrative embodiment 12, wherein fine-tuning the trained machine learning based model for performing the medical imaging analysis task based on the one or more training medical images, the ground truth labels, and the generated pseudo labels comprises: fine-tuning the trained machine learning based model to maximize an overlap between a predicted location of the one or more anatomical objects and a location defined in the ground truth labels.

Illustrative embodiment 14. The non-transitory computer-readable storage medium according to any one of illustrative embodiments 12-13, wherein fine-tuning the trained machine learning based model for performing the medical imaging analysis task based on the one or more training medical images, the ground truth labels, and the generated pseudo labels comprises: fine-tuning the trained machine learning based model to maximize an overlap between a predicted location of unlabeled anatomical objects and a location defined in the pseudo labels for the unlabeled anatomical objects.

Illustrative embodiment 15. The non-transitory computer-readable storage medium according to any one of illustrative embodiments 12-14, wherein the medical imaging analysis task is segmentation.

Illustrative embodiment 16. A computer-implemented method comprising: receiving one or more training medical images and ground truth labels identifying one or more anatomical objects in the one or more training medical images; training a machine learning based model for performing a medical imaging analysis task based on the one or more training medical images and the ground truth labels; generating pseudo labels identifying the one or more anatomical objects in the one or more training medical images using the trained machine learning based model; fine-tuning the trained machine learning based model for performing the medical imaging analysis task based on the one or more training medical images, the ground truth labels, and the generated pseudo labels; and outputting the fine-tuned machine learning based model.

Illustrative embodiment 17. The computer-implemented method according to illustrative embodiment 16, further comprising: filtering the generated pseudo labels based on a comparison between 1) each of the generated pseudo labels identifying a particular anatomical object in the one or more training medical images and 2) a distribution of the ground truth labels identifying the particular anatomical object in the one or more training medical images, wherein fine-tuning the trained machine learning based model for performing the medical imaging analysis task based on the one or more training medical images, the ground truth labels, and the generated pseudo labels comprises fine-tuning the trained machine learning based model for performing the medical imaging analysis task based on the filtered pseudo labels.

Illustrative embodiment 18. The computer-implemented method according to any one of illustrative embodiments 16-17, wherein filtering the generated pseudo labels based on a comparison between 1) each of the generated pseudo labels identifying a particular anatomical object in the one or more training medical images and 2) a distribution of the ground truth labels identifying the particular anatomical object in the one or more training medical images comprises: determining a feature representation of each of the generated pseudo labels using a feature extractor model of the machine learning based model; determining a distance between a) the feature representation of each of the generated pseudo labels identifying the particular anatomical object in the one or more training medical images and b) the distribution of the ground truth labels identifying the particular anatomical object in the one or more training medical images; and filtering the generated pseudo labels based on a comparison between the distances and a threshold.

Illustrative embodiment 19. The computer-implemented method according to any one of illustrative embodiments 16-18, wherein fine-tuning the trained machine learning based model for performing the medical imaging analysis task based on the one or more training medical images, the ground truth labels, and the generated pseudo labels comprises: fine-tuning the trained machine learning based model to maximize an overlap between a predicted location of the one or more anatomical objects and a location defined in the ground truth labels.

Illustrative embodiment 20. The computer-implemented method according to any one of illustrative embodiments 16-19, wherein fine-tuning the trained machine learning based model for performing the medical imaging analysis task based on the one or more training medical images, the ground truth labels, and the generated pseudo labels comprises: fine-tuning the trained machine learning based model to maximize an overlap between a predicted location of unlabeled anatomical objects and a location defined in the pseudo labels for the unlabeled anatomical objects.

The invention claimed is:

1. A computer-implemented method comprising:
receiving one or more input medical images;
performing a medical imaging analysis task based on the one or more input medical images using a machine learning based model; and
outputting results of the medical imaging analysis task, wherein the machine learning based model is trained by:
receiving one or more training medical images and ground truth labels identifying one or more anatomical objects in the one or more training medical images,
training the machine learning based model for performing the medical imaging analysis task based on the one or more training medical images and the ground truth labels,
generating pseudo labels identifying the one or more anatomical objects in the one or more training medical images using the trained machine learning based model,
filtering the generated pseudo labels based on a comparison between 1) each of the generated pseudo labels identifying a particular anatomical object in the one or more training medical images and 2) a distribution of the ground truth labels identifying the particular anatomical object in the one or more training medical images, and
fine-tuning the trained machine learning based model for performing the medical imaging analysis task based on the one or more training medical images, the ground truth labels, and the filtered pseudo labels.

2. The computer-implemented method of claim 1, wherein filtering the generated pseudo labels based on a comparison between 1) each of the generated pseudo labels identifying a particular anatomical object in the one or more training medical images and 2) a distribution of the ground truth labels identifying the particular anatomical object in the one or more training medical images comprises:
determining a feature representation of each of the generated pseudo labels using a feature extractor model of the machine learning based model;
determining a distance between a) the feature representation of each of the generated pseudo labels identifying the particular anatomical object in the one or more training medical images and b) the distribution of the ground truth labels identifying the particular anatomical object in the one or more training medical images; and
filtering the generated pseudo labels based on a comparison between the distances and a threshold.

3. The computer-implemented method of claim 1, wherein the machine learning based model is further trained by:
repeating the generating, the filtering, and the fine-tuning for a plurality of iterations.

4. The computer-implemented method of claim 1, wherein fine-tuning the trained machine learning based model for performing the medical imaging analysis task based on the one or more training medical images, the ground truth labels, and the filtered pseudo labels comprises:
fine-tuning the trained machine learning based model to maximize an overlap between a predicted location of the one or more anatomical objects and a location defined in the ground truth labels.

5. The computer-implemented method of claim 1, wherein fine-tuning the trained machine learning based model for performing the medical imaging analysis task based on the one or more training medical images, the ground truth labels, and the filtered pseudo labels comprises:
fine-tuning the trained machine learning based model to maximize an overlap between a predicted location of unlabeled anatomical objects and a location defined in the filtered pseudo labels for the unlabeled anatomical objects.

6. The computer-implemented method of claim 1, wherein the medical imaging analysis task is segmentation.

7. An apparatus comprising:
means for receiving one or more input medical images;
means for performing a medical imaging analysis task based on the one or more input medical images using a machine learning based model; and
means for outputting results of the medical imaging analysis task,
wherein the machine learning based model is trained by:
receiving one or more training medical images and ground truth labels identifying one or more anatomical objects in the one or more training medical images, training the machine learning based model for perform-
ing the medical imaging analysis task based on the
one or more training medical images and the ground
truth labels, generating pseudo labels identifying the one or more
anatomical objects in the one or more training medi-
cal images using the trained machine learning based
model, filtering the generated pseudo labels based on a com-
parison between 1) each of the generated pseudo
labels identifying a particular anatomical object in
the one or more training medical images and 2) a
distribution of the ground truth labels identifying the
particular anatomical object in the one or more
training medical images, and fine-tuning the trained machine learning based model
for performing the medical imaging analysis task
based on the one or more training medical images,
the ground truth labels, and the filtered pseudo
labels.

8. The apparatus of claim 7, wherein filtering the gener-
ated pseudo labels based on a comparison between 1) each
of the generated pseudo labels identifying a particular ana-
tomical object in the one or more training medical images
and 2) a distribution of the ground truth labels identifying
the particular anatomical object in the one or more training
medical images comprises:

determining a feature representation of each of the gen-
erated pseudo labels using a feature extractor model of
the machine learning based model;

determining a distance between a) the feature represen-
tation of each of the generated pseudo labels identify-
ing the particular anatomical object in the one or more
training medical images and b) the distribution of the
ground truth labels identifying the particular anatomi-
cal object in the one or more training medical images;
and filtering the generated pseudo labels based on a compari-
son between the distances and a threshold.

9. The apparatus of claim 7, wherein the machine learning
based model is further trained by:

repeating the generating, the filtering, and the fine-tuning
for a plurality of iterations.

10. A non-transitory computer-readable storage medium
comprising instructions which, when executed by a com-
puter, cause the computer to carry out operations compris-
ing:

receiving one or more input medical images;

performing a medical imaging analysis task based on the
one or more input medical images using a machine
learning based model; and outputting results of the medical imaging analysis task, wherein the machine learning based model is trained by:

receiving one or more training medical images and
ground truth labels identifying one or more anatomi-
cal objects in the one or more training medical
images, training the machine learning based model for perform-
ing the medical imaging analysis task based on the
one or more training medical images and the ground
truth labels, generating pseudo labels identifying the one or more
anatomical objects in the one or more training medi-
cal images using the trained machine learning based
model, filtering the generated pseudo labels based on a com-
parison between 1) each of the generated pseudo labels identifying a particular anatomical object in
the one or more training medical images and 2) a
distribution of the ground truth labels identifying the
particular anatomical object in the one or more
training medical images, and fine-tuning the trained machine learning based model
for performing the medical imaging analysis task
based on the one or more training medical images,
the ground truth labels, and the filtered pseudo
labels.

11. The non-transitory computer-readable storage
medium of claim 10, wherein fine-tuning the trained
machine learning based model for performing the medical
imaging analysis task based on the one or more training
medical images, the ground truth labels, and the filtered
pseudo labels comprises:

fine-tuning the trained machine learning based model to
maximize an overlap between a predicted location of
the one or more anatomical objects and a location
defined in the ground truth labels.

12. The non-transitory computer-readable storage
medium of claim 10, wherein fine-tuning the trained
machine learning based model for performing the medical
imaging analysis task based on the one or more training
medical images, the ground truth labels, and the filtered
pseudo labels comprises:

fine-tuning the trained machine learning based model to
maximize an overlap between a predicted location of
unlabeled anatomical objects and a location defined in
the filtered pseudo labels for the unlabeled anatomical
objects.

13. The non-transitory computer-readable storage
medium of claim 10, wherein the medical imaging analysis
task is segmentation.

14. A computer-implemented method comprising:

receiving one or more training medical images and
ground truth labels identifying one or more anatomical
objects in the one or more training medical images;

training a machine learning based model for performing a
medical imaging analysis task based on the one or more
training medical images and the ground truth labels;

generating pseudo labels identifying the one or more
anatomical objects in the one or more training medical
images using the trained machine learning based
model;

filtering the generated pseudo labels based on a compari-
son between 1) each of the generated pseudo labels
identifying a particular anatomical object in the one or
more training medical images and 2) a distribution of
the ground truth labels identifying the particular ana-
tomical object in the one or more training medical
images;

fine-tuning the trained machine learning based model for
performing the medical imaging analysis task based on
the one or more training medical images, the ground
truth labels, and the filtered pseudo labels; and outputting the fine-tuned machine learning based model.

15. The computer-implemented method of claim 14,
wherein filtering the generated pseudo labels based on a
comparison between 1) each of the generated pseudo labels
identifying a particular anatomical object in the one or more
training medical images and 2) a distribution of the ground
truth labels identifying the particular anatomical object in
the one or more training medical images comprises:

determining a feature representation of each of the gen-
erated pseudo labels using a feature extractor model of
the machine learning based model;

determining a distance between a) the feature represen-
tation of each of the generated pseudo labels identify-
ing the particular anatomical object in the one or more
training medical images and b) the distribution of the
ground truth labels identifying the particular anatomical object in the one or more training medical images;
and filtering the generated pseudo labels based on a compari-
son between the distances and a threshold.

16. The computer-implemented method of claim 14, wherein fine-tuning the trained machine learning based
model for performing the medical imaging analysis task
based on the one or more training medical images, the
ground truth labels, and the filtered pseudo labels comprises:

fine-tuning the trained machine learning based model to
maximize an overlap between a predicted location of
the one or more anatomical objects and a location
defined in the ground truth labels.

17. The computer-implemented method of claim 14,
wherein fine-tuning the trained machine learning based
model for performing the medical imaging analysis task
based on the one or more training medical images, the
ground truth labels, and the filtered pseudo labels comprises:

fine-tuning the trained machine learning based model to
maximize an overlap between a predicted location of
unlabeled anatomical objects and a location defined in
the filtered pseudo labels for the unlabeled anatomical
objects.

\*  \*  \*  \*  \*